(12) United States Patent
Yamato et al.

(10) Patent No.: US 6,485,886 B1
(45) Date of Patent: Nov. 26, 2002

(54) OXIME DERIVATIVES AND THE USE THEREOF AS LATENT ACIDS

(75) Inventors: Hitoshi Yamato, Hyogo (JP); Toshikage Asakura, Minoo (JP); Jean-Luc Birbaum, Binningen (CH); Kurt Dietliker, Allschwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/830,248

(22) PCT Filed: Oct. 18, 1999

(86) PCT No.: PCT/EP99/07876
§ 371 (c)(1),
(2), (4) Date: Apr. 23, 2001

(87) PCT Pub. No.: WO00/26219
PCT Pub. Date: May 11, 2000

(30) Foreign Application Priority Data

Oct. 29, 1998 (EP) .............................. 98811084

(51) Int. Cl.[7] .......................... G03C 1/73; G03F 7/004; G03F 7/075; C07D 333/26; C07C 251/58; C07C 251/62; C07F 9/11; C07F 9/17; C07F 7/10; C08K 5/45; C08K 5/521; C08K 5/5475

(52) U.S. Cl. ............................ 430/270.1; 430/281.1; 430/913; 430/916; 430/919; 522/26; 522/33; 522/39; 522/53; 522/63; 522/126; 548/112; 548/413; 548/558; 548/565; 549/6; 549/29; 549/61; 549/68; 549/474; 549/479; 549/480; 558/405; 558/408; 564/253; 564/254; 564/265

(58) Field of Search .................. 430/281.1, 270.1, 430/913, 916, 919; 522/26, 33, 39, 53, 63, 126; 548/112, 413, 558, 565; 549/6, 29, 61, 68, 474, 479, 480; 558/405, 408; 564/253, 254, 265

(56) References Cited

U.S. PATENT DOCUMENTS

| | | |
|---|---|---|
| 4,540,598 A | 9/1985 | Berner et al. ............. 427/54.1 |
| 5,627,011 A | 5/1997 | Münzel et al. ........... 430/270.1 |
| 5,714,625 A | 2/1998 | Hada et al. ................ 558/437 |
| 5,928,837 A | 7/1999 | Sato et al. ............... 430/270.1 |
| 6,004,724 A | 12/1999 | Yamato et al. ........... 430/281.1 |
| 6,017,675 A | 1/2000 | Dietliker et al. ......... 430/270.1 |

FOREIGN PATENT DOCUMENTS

| | | |
|---|---|---|
| EP | 0571330 | 11/1993 |
| EP | 0848289 | 6/1998 |
| FR | 2740455 | 4/1997 |
| GB | 2306958 | 5/1997 |
| WO | 98/10335 | 3/1998 |
| WO | 99/01429 | 1/1999 |
| WO | WO 2000/026219 | * 5/2000 |
| WO | WO 2000/053530 | * 9/2000 |

OTHER PUBLICATIONS

Derwent Abstr. 1997–461780 for JP 09211846 (1997).
Derwent Abstr. 1997–263428 for JP 09090627 (1997).
Derwent Abstr. 1993–033456 for JP 04362647 (1992).
R. Davis et al., J. Chem. Eng. Data, vol. 8, p. 580, (1963).

* cited by examiner

Primary Examiner—Susan W. Berman
(74) Attorney, Agent, or Firm—David R. Crichton

(57) ABSTRACT

New oxime derivatives of formula (I) or. (II), wherein m is 0 or 1; $R_1$ inter alia is phenyl, naphthyl, anthracyl, phenanthryl or a heteroaryl radical; $R'_1$ is for example $C_2$–$C_{12}$alkylene, phenylene, naphthylene; $R_2$ is CN; $R_3$ is $C_2$–$C_6$haloalkanoyl, halobenzoyl, a phosphoryl or an organosilyl group; $R_4$, $R_5$, $R_{10}$ and $R_{11}$ inter alia are hydrogen, $C_1$–$C_6$alkyl, $C_1$–$C_6$alkoxy; $R_6$ inter alia is hydrogen phenyl, $C_1$–$C_{12}$alkyl; $R_7$ and $R_8$ inter alia are hydrogen, $C_1$–$C_{12}$alkyl; or $R_7$ and $R_8$, together with the nitrogen atom to which they are bonded, form a 5-, 6 or 7-membered ring; $R_9$ is for example $C_1$–$C_{12}$alkyl; and A inter alia is S, O, $NR_{7a}$; are useful as latent acids, especially in photoresist applications.

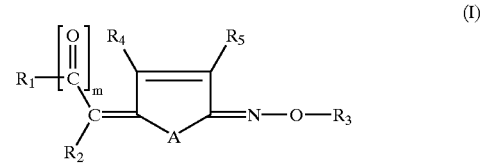

(I)

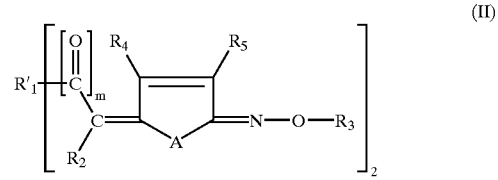

(II)

17 Claims, No Drawings

OXIME DERIVATIVES AND THE USE THEREOF AS LATENT ACIDS

The invention relates to new oxime derivatives, photopolymerisable compositions comprising said compounds and to the use of the compounds as latent acids, which can be activated by irradiation with light.

In U.S. Pat. No. 4,540,598 surface-coating compositions based on photosensitive oxime sulfonates and customary acid-curable resins are disclosed. In EP 571330 the use of α-(4-toluene-sulfon-yloxyimino)-4-methoxybenzyl cyanide and α-(4-toluene-sulfonyloxyimino)-3-thienylmethyl cyanide as latent acid donors in positive and negative photoresists for wavelengths of 340–390 nm, especially those in the radiation region of the mercury i line (365 nm) is described. In GB 2306958 the use of oxime-sulfonates as latent acid donors in positive and negative photoresists for wavelengths between 180 and 600 nm, especially those in the radiation region beyond 390 nm is reported. In U.S. Pat. No. 5,714,625 non-aromatic α-(alkylsulfonyloxyimino)-1-cyclohexenylacetonitriles and α-(alkylsulfonyloxyimino)-1-cyclopentenylacetonitriles are disclosed. The preparation of several quinone oxime compounds is described by Ralph B. Davies et al. in J. Chem. Eng. Data 8, 580 (1963).

In the art, a need still exists, especially for reactive non-ionic latent acid donors that are thermally and chemically stable and that, after being activated by light, can be used as catalysts for a variety of acid-catalysed reactions, such as polycondensation reactions, acid-catalysed depolymerisation reactions, acid-catalysed electrophilic substitution reactions or the acid-catalysed removal of protecting groups. There is also a need for compounds that when irradiated with light are converted into acids and are capable of acting as solubility inhibitors in resist formulations. Furthermore there is a need for photolatent acids which can be bleached upon irradiation.

Surprisingly, it has now been found that specific oxime derivatives are especially suitable as catalysts for such reactions. The optical absorption spectra of the specific compounds of the invention are particularly tunable over a wide range of the electromagnetic spectrum. Furthermore they can be bleached upon irradiation.

Accordingly, the present invention pertains to compounds of the formula I and II

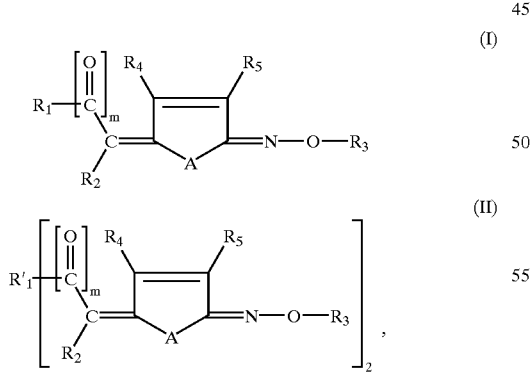

wherein
m is 0 or 1;
$R_1$ is phenyl which is unsubstituted or substituted by one or more of the radicals $C_1$–$C_{12}$alkyl, $C_1$–$C_4$haloalkyl, halogen, phenyl, $OR_6$, $NR_7R_8$, $SR_9$ and/or —S-phenyl, optionally the substituents $OR_6$, $SR_9$ or $NR_7R_8$ form 5- or 6-membered rings, via the radicals $R_6$, $R_7$, $R_8$ and/or $R_9$, with further substituents on the phenyl ring or with one of the carbon atoms of the phenyl ring, or $R_1$ is naphthyl, anthracyl or phenanthryl, the radicals naphthyl, anthracyl and phenanthryl being unsubstituted or substituted by $C_1$–$C_6$alkyl, phenyl, $OR_6$, $NR_7R_8$, $SR_9$ and/or —S-phenyl, optionally the substituents $OR_6$, $SR_9$ or $NR_7R_8$ form 5- or 6-membered rings, via the radicals $R_6$, $R_7$, $R_8$ and/or $R_9$ with further substituents on the naphthyl, anthracyl or phenanthryl ring or with one of the carbon atoms of the naphthyl, anthracyl or phenanthryl ring, or $R_1$ is a heteroaryl radical which is unsubstituted or substituted by $C_1$–$C_6$alkyl, phenyl, $OR_6$, $NR_7R_8$, $SR_9$ and/or —S-phenyl, optionally the substituents $OR_6$, $SR_9$ or $NR_7R_8$ form 5- or 6-membered rings, via the radicals $R_6$, $R_7$, $R_8$ and/or $R_9$ with further substituents on the heteroaryl ring or with one of the carbon atoms of the heteroaryl ring, or, if m is 0, $R_1$ additionally is $C_2$–$C_6$alkoxycarbonyl, phenoxycarbonyl, CN, hydrogen or $C_1$–$C_{12}$ alkyl;
$R'_1$ is $C_2$–$C_{12}$alkylene, phenylene, naphthylene,

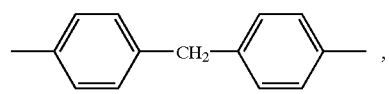

diphenylene or oxydiphenylene, these radicals being unsubstituted or substituted by $C_1$–$C_{12}$alkyl;
$R_2$ is CN;
n is 1 or 2;
$R_3$ is $C_2$–$C_6$haloalkanoyl, halobenzoyl, or a group

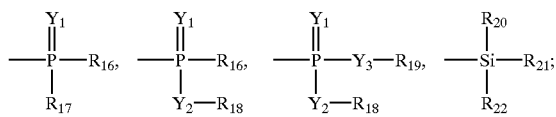

$Y_1$, $Y_2$ and $Y_3$ are independently of each other O or S;
$R_4$ and $R_5$ are independently of each other hydrogen, halogen, $C_1$–$C_6$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_6$, $SR_9$, $NR_7R_8$, $C_2$–$C_6$-alkoxycarbonyl, phenoxycarbonyl, $S(O)_nC_1$–$C_6$alkyl, $S(O)_nC_6$–$C_{12}$aryl, $C_1$–$C_{12}$alkyl-substituted $S(O)_n$ $C_6$–$C_{12}$aryl, $SO_2O$—$C_1$–$C_6$alkyl, $SO_2O$—$C_6$–$C_{10}$aryl or $NHCONH_2$, or $R_4$ and $R_5$ together are —$C(R_{12})$=$C(R_{13})$—$C(R_{14})$=$C(R_{15})$—;
$R_6$ is hydrogen, phenyl; $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$-alkanoyl; or $R_6$ is $C_2$–$C_{12}$alkyl interrupted by —O—, optionally substituted by phenyl, OH, $C_1$–$C_{12}$-alkoxy, $C_1$–$C_{12}$alkylsulfonyl, phenylsulfonyl, (4-methylphenyl)sulfonyl and/or by $C_2$–$C_6$alkanoyl;
$R_7$ and $R_8$ are independently of each other hydrogen; $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_7$ and $R_8$ are $C_2$–$C_{12}$alkyl interrupted by —O—, optionally substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_7$ and $R_8$, together with the nitrogen atom to which they are bound, form a 5-, 6- or 7-membered ring which optionally is interrupted by —O— or by —$NR_{7a}$—;

$R_{7a}$ is hydrogen, phenyl; $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$-alkanoyl; or $R_{7a}$ is $C_2$–$C_{12}$alkyl interrupted by —O—, optionally substituted by phenyl, OH, $C_1$–$C_{12}$alkoxy, $C_1$–$C_{12}$alkylsulfonyl, phenylsultonyl, (4-methylphenyl)sulfonyl and/or by $C_2$–$C_6$-alkanoyl: or $R_{7a}$ is phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl;

$R_9$ is $C_1$–$C_{12}$alkyl which is unsubstituted or substituted by OH and/or $C_1$–$C_4$alkoxy; or $C_2$–$C_{12}$-alkyl interrupted by —O—, soptionally substituted by OH and/or $C_1$–$C_4$alkoxy;

A is S, O, $NR_{7a}$, or a group of formula A1, A2, A3 or A4

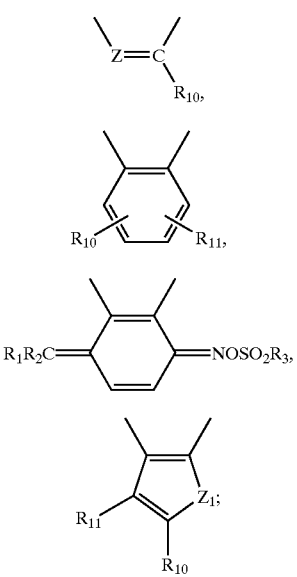

$R_{10}$ and $R_{11}$ independently of each other have one of the meanings given for $R_4$, or $R_{10}$ and $R_{11}$ together are —CO—$NR_{7a}$CO—, or $R_{10}$ and $R_{11}$ together are —$C(R_{12})$=$C(R_{13})$—$C(R_{14})$=$C(R_{15})$—;

$R_{12}$, $R_{13}$, $R_{14}$ and $R_{15}$ independently of one another are hydrogen, $C_1$–$C_4$alkyl, halogen, phenyl, $OR_6$, $SR_9$, $NR_7R_8$, —S-phenyl, $C_2$–$C_6$alkoxycarbonyl, phenoxycarbonyl, CN, $NO_2$, $C_1$–$C_4$haloalkyl, $S(O)_nC_1$–$C_6$alkyl, $S(O)_nC_6$–$C_{12}$aryl, $C_1$–$C_{12}$alkyl-substituted $S(O)_nC_6$–$C_{12}$aryl, $SO_2O$—$C_1$–$C_6$alkyl, $SO_2O$—$C_6$–$C_{10}$aryl or $NHCONH_2$;

$R_{16}$ and $R_{17}$ independently of each other are $C_1$–$C_6$alkyl which is unsubstituted or substituted by halogen; or are phenyl which is unsubstituted or substituted by $C_1$–$C_4$alkyl or halogen; $R_{18}$ and $R_{19}$ independently of each other have one of the meanings of $R_{16}$, or $R_{18}$ and $R_{19}$, or together are 1,2-phenylene or $C_2$–$C_6$alkylene which is unsubstituted or substituted by $C_1$–$C_4$alkyl or halogen;

$R_{20}$, $R_{21}$ and $R_{22}$ independently of each other are $C_1$–$C_6$alkyl which is unsubstituted or substituted by halogen; or are phenyl which is unsubstituted or substituted by $C_1$–$C_4$alkyl or halogen; or $R_{21}$ and $R_{22}$ together are 2,2'-biphenylene or $C_2$–$C_6$alkylene which is unsubstituted or substituted by $C_1$–$C_4$alkyl or halogen;

Z is $CR_{11}$ or N; and $Z_1$ is —$CH_2$—, S, O or $NR_{7a}$.

$C_1$–$C_{12}$alkyl is linear or branched and is, for example, $C_1$–$C_8$—, $C_1$–$C_6$— or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl or dodecyl, especially $C_1$–$C_6$alkyl, preferably $C_1$–$C_4$alkyl, such as methyl, isopropyl or butyl. Of interest are, for example, $C_1$–$C_8$-, especially $C_1$–$C_6$-, preferably $C_1$–$C_4$-alkyl, such as methyl or butyl.

$C_2$–$C_{12}$alkyl, which is interrupted once or several times by —O— or by —$NR_{7a}$—, is interrupted, for example, from one to five times, for example from one to three times or once or twice, by —O— or —$NR_{7a}$—. This results in structural units as for example: —$O(CH_2)_2OCH_3$, —$O(CH_2CH_2O)_2CH_2CH_3$, —$CH_2$—O—$CH_3$, —$CH_2CH_2$—O—$CH_2CH_3$, —$[CH_2CH_2O]y$—$CH_3$, wherein y is an integer of 1–5, —$(CH_2CH_2O)_5CH_2CH_3$, —$CH_2$—$CH(CH_3)$—O—$CH_2$—$CH_2CH_3$ or —$CH_2$—CH$(CH_3)$—O—$CH_2$—$CH_3$.

$C_2$–$C_{12}$Alkylene is linear or branched and is, for example, $C_2$–$C_8$-, $C_2$–$C_6$- or $C_2$–$C_4$-alkylene Examples are ethylene, propylene, butylene, pentylene, hexylene, heptylene, octylene, nonylene, decylene, undecylene and dodecylene, especially $C_1$–$C_6$alkylene, preferably $C_1$–$C_4$-alkylene, such as methylene or butylene.

Substituted phenyl carries from one to five, for example one, two or three, especially one or two, substituents on the phenyl ring. The substitution is, for example in the 2-, 3-, 4-, 6-, 3,4-, 2,6-, 2,4-, 2,4,6- or 3,4,5-position of the phenyl ring. When the radicals naphthyl, phenanthryl, heteroaryl and anthracyl are substituted by one or more radicals, they are, for example, mono- to penta-substituted, for example mono-, di- or tri-substituted, especially mono- or di-substituted.

When $R_1$ is a phenyl radical substituted by $OR_6$, $NR_7R_8$ and/or by $SR_9$ and the substituents $OR_6$, $NR_7R_8$ or $SR_9$ form 5- or 6-membered rings, via the radicals $R_6$, $R_7$, $R_8$ or $R_9$, with other substituents on the phenyl ring or with one of the carbon atoms of the phenyl ring, for example the following structural units are obtained

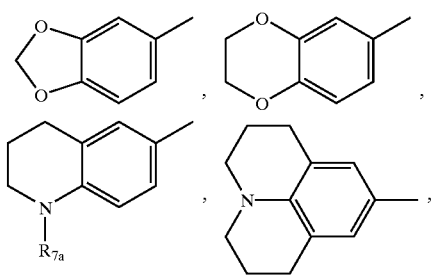

wherein $R_{7a}$ is as defined above.

In the present application, the term "heteroaryl" denotes unsubstituted and substituted radical, for example 2-thienyl,

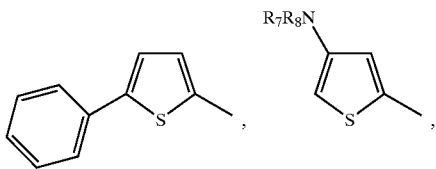

wherein R₇ and R₈ are as defined above, thianthrenyl, isobenzofuranyl, xanthenyl, phenoxanthiinyl,

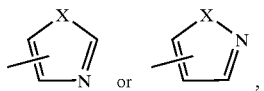

wherein X is S, O or $NR_{7a}$ and $R_{7a}$ is as defined above. Examples thereof are pyrazolyl, thiazolyl, oxazolyl, isothiazolyl or isoxazolyl. Also included are, for example, furyl, pyrrolyl, 1,2,4-triazolyl,

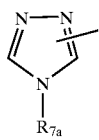

or 5-membered ring heterocycles having a fused-on aromatic group, for example benzimidazolyl, benzothienyl, benzofuranyl, benzoxazolyl and benzothiazolyl.

Other examples of "heteroaryls" are pyridyl, especially 3-pyridyl,

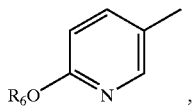

wherein $R_6$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

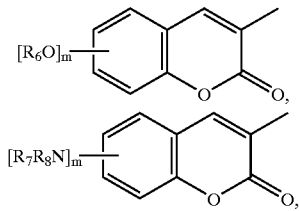

wherein $R_6$, $R_7$, $R_8$ and m are as defined above,

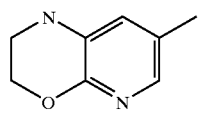

or anthraquinonyl. Each of the heteroaryls may carry the substituents indicated above or in claim 1.

$C_1$–$C_6$Alkanoyl is, for example, formyl, acetyl, propionyl, butanoyl or hexanoyl, especially acetyl.

$C_1$–$C_{12}$Alkoxy is a linear or branched radical and is $C_1$–$C_8$-, $C_1$–$C_6$-, $C_1$–$C_4$alkoxy, for example, methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, isobutyloxy or tert-butyloxy, preferably methoxy. $C_1$–$C_6$alkoxy is has the same meanings as given above up to the corresponding number of C-atoms.

$C_2$–$C_6$Alkoxycarbonyl is ($C_1$–$C_5$alkyl)—O—C(O)—, wherein $C_1$–$C_5$alkyl is as defined above up to the appropriate number of carbon atoms. Examples are methoxycarbonyl, ethoxycarbonyl, propoxycarbonyl, butoxycarbonyl or pentyloxycarbonyi, wherein the alkyl radicals having more than two carbon atoms are linear or branched.

$C_1$–$C_4$haloalkyl is $C_1$–$C_4$alkyl mono- or poly-substituted by halogen, $C_1$–$C_4$alkyl is as defined above. There are, for example, from one to three or one or two halogen substituents at the alkyl radical. Examples are chloromethyl, trichloromethyl, trifluoromethyl or 2-bromopropyl, especially trifluoromethyl or trichloromethyl.

$C_2$–$C_6$haloalkanoyl is ($C_1$–$C_5$haloalkyl)—C(O)—, wherein $C_1$–$C_5$haloalkyl is linear or branched $C_1$–$C_5$alkyl mono- or poly-substituted by halogen. Examples are chloroacetyl, trichloroacetyl, trifluoroacetyl, pentafluoropropionyl, perfluorooctanoyl, or 2-bromopropionyl, especially trifluoroacetyl or trichloroacetyl.

Halobenzoyl is benzoyl which is mono- or poly-substituted by halogen and/or $C_1$–$C_4$haloalkyl, wherein $C_1$–$C_4$haloalkyl is as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine.

In a group $S(O)_n$—$C_6$–$C_{10}$aryl which is unsubstituted or substituted by $C_1$–$C_{12}$alkyl, the aryl radical is, for example, phenyl, tosyl, dodecylphenyl or 1- or 2-naphthyl.

Phenyl—$C_1$–$C_3$alkyl is, for example, benzyl, 2-phenylethyl, 3-phenylpropyl, a-methylbenzyl or α,α-dimethylbenzyi, especially benzyl.

Diphenylphosphinoyl is

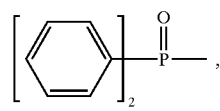

oxydiphenylene is

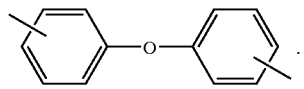

When R₇ and R₈ together with the nitrogen atom to which they are bound form a 5-, 6- or 7-membered ring that may be interrupted by —O— or by —$NR_{7a}$—, for example the following structures are obtained

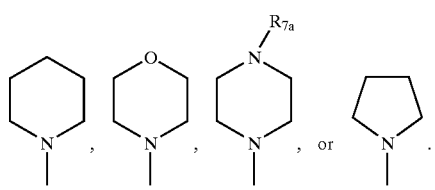

When R₄ and R₅ together are —(CR₁₂)=C(R₁₃)—C(R₁₄)=C(R₁₅)— the following structures are formed

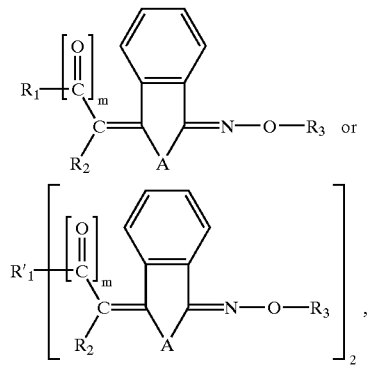

wherein R₁, R₂,
  m, R₃, R'₁ and A are as defined above or in claim 1.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

Preference is given to compounds of formula I and II, wherein
  m is 0;
  R₁ is phenyl which is unsubstituted or substituted by C₁–C₆alkyl, phenyl, OR₆, SR₉, —S-phenyl, halogen and/or by NR₇R₈; optionally the substituents OR₆, or NR₇R₈ form 5- or 6-membered rings, via the radicals R₆, R₇ and/or R₉ with further substituents of the phenyl ring, or with one of the carbon atoms of the phenyl ring;
  R'₁ is phenylene, naphthylene,

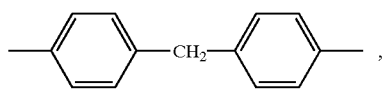

diphenylene or oxydiphenylene, these radicals being unsubstituted or substituted by C₁–C₁₂alkyl.

Most preferred are compounds of formula Ia,

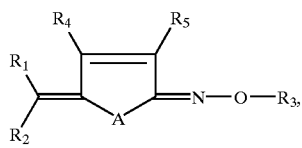

(Ia)

wherein
  R₁, R₂, R₃, R₄, R₅ and A are as defined in claim 1.
Compounds of formula Ia, wherein R₃ is a group

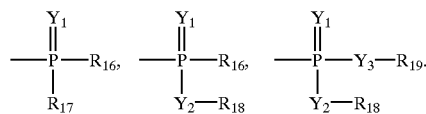

and
  Y₁, Y₂, Y₃ R₁₆, R₁₇ R₁₈ and R₁₉ are as defined in claim 1.

In particular preferred are compounds of formula Ia, wherein
  R₁ is phenyl which is unsubstituted or substituted once or twice by C₁–C₄alkyl, OR₆ or halogen;
  R₂ is CN;
  R₃ is C₂–C₆haloalkanoyl, halobenzoyl, or a group

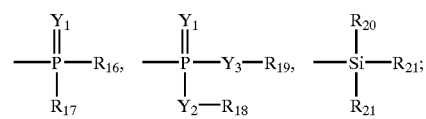

Y₁, Y₂ and Y₃ are independently of each other O or S;
  R₄ and R₅ are hydrogen;
  R₆ is C₁–C₃alkyl
  A is —S— or a group of the formula A₁

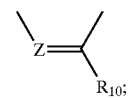

Z is CR₁₁;
  R₁₀ and R₁₁ are hydrogen;
  R₁₆ and R₁₇ independently of each other are phenyl;
  R₁₈ and R₁₉ independently of each other are C₁–C₆alkyl or phenyl; and
  R₂₀, R₂₁, and R₂₂ are phenyl.

Preferred are compounds of formula Ia.

Further compounds of interest are those of formula Ia, wherein
  R₁ is a heteroaryl radical which is unsubstituted or mono- or poly-substituted by C₁–C₆alkyl, phenyl, OR₆, SR₉, —S-phenyl and/or by NR₇R₈; optionally the substituents OR₆ or NR₇R₈ form 5- or 6-membered rings, via the radicals R₆, R₇ and/or R₈, with further substituents or with one of the carbon atoms of the heteroaryl ring.

Further compounds of interest are those of the formula II, wherein R'₁ is phenylene, naphthylene,

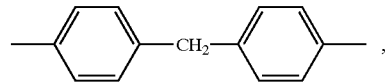

diphenylene or oxydiphenylene, the radicals phenylene, naphthylene,

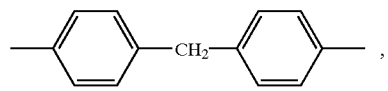

diphenylene and oxydiphenylene being unsubstituted or substituted by $C_1$–$C_{12}$alkyl;

Other examples of compounds are those of formula Ia or II wherein $R_1$ is CN, $C_2$–$C_6$alkoxycarbonyl, $C_1$–$C_4$haloalkyl, $S(O)_nC_1$–$C_6$alkyl, $S(O)_n$—$C_6$–$C_{10}$aryl or $C_1$–$C_{12}$alkyl-substituted $S(O)_n$—$C_6$–$C_{10}$aryl.

Most preferred compounds are those of formula Ia or II, wherein $R_1$ is phenyl (substituted as defined above and in claim 1) or a heteroaryl radical (substituted as defined above and in claim 1) and $R_2$ is CN.

Preference is given especially to compounds of formula Ia and II wherein $R_6$ is $C_1$–$C_6$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or by $C_2$–$C_6$alkanoyl; or $R_6$ is $C_2$–$C_6$alkyl which is interrupted by —O—, optionally substituted by OH, $C_1$–$C_4$alkoxy, $C_1$–$C_{12}$alkylsulfonyl, phenyisulfonyl, (4-methylphenyl)sulfonyl and/or by $C_2$–$C_6$alkanoyl.

Preference is given also to compounds of formula Ia and II wherein $R_3$ is $C_2$–$C_6$haloalkanoyl, halobenzoyl, or a group

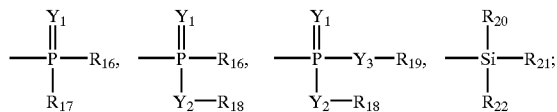

$Y_1$, $Y_2$ and $Y_3$ independently of each other are O or S; $R_{16}$ and $R_{17}$ independently of each other are $C_1$–$C_6$alkyl; phenyl which is unsubstituted or substituted by $C_1$–$C_4$alkyl; $R_{18}$ and $R_{19}$ independently of each other are $C_1$–$C_6$alkyl; phenyl which is unsubstituted or substituted by $C_1$–$C_4$alkyl; $R_{20}$, $R_{21}$ and $R_{22}$ independently of each other are $C_1$–$C_6$alkyl; phenyl which is unsubstituted or substituted by $C_1$–$C_4$alkyl.

Preference is given likewise to compounds of formula Ia and II wherein $R_4$ and $R_5$ are independently of each other hydrogen, halogen, $C_1$–$C_6$alkyl, $C_1$–$C_6$alkoxy, $C_1$–$C_4$haloalkyl, $NO_2$, $C_2$–$C_6$alkanoyl, benzoyl, or $OR_6$, or $R_4$ and $R_5$ together are —CH=CH—CH=CH—;

$R_7$ and $R_8$ are independently of each other hydrogen; or $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or by $C_1$–$C_6$alkanoyl; or $R_7$ and $R_8$ are $C_2$–$C_{12}$alkyl interrupted by —O—, optionally substituted by OH, $C_1$–$C_4$alkoxy, $C_1$–$C_{12}$alkylsulfonyl, phenylsulfonyl, (4-methylphenyl)sulfonyl and/or by $C_1$–$C_6$alkanoyl;

or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_7$ and $R_8$, together with the nitrogen atom to which they are bound, form a 5-, 6- or 7-membered ring which optionally is interrupted by —O— or by —$NR_{7a}$—; and $R_9$ is $C_1$–$C_{12}$alkyl which is unsubstituted or substituted by OH and/or by $C_1$–$C_4$alkoxy or $R_9$ is $C_2$–$C_{12}$alkyl interrupted by —O—, optionally substituted by OH and/or by $C_1$–$C_4$alkoxy;

A is S, O, $NR_{7a}$, or a group of formula A1, A2 or A3;

$R_{10}$ and $R_{11}$ independently of each other have one of the meanings of $R_4$; and Z is $CR_{11}$ or N.

Specific examples of compounds according to the present invention are (4-Diethoxyphosphoryloxyimino-cyclohexa-2,5-dienylidene)-phenyl-acetonitrile; (4-Diphenoyphosphoryloxyimino-cyclohexa-2,5-dienylidene)-phenyl-acetonitrile; (4-Diethoxythiophosphoryloxyimino-cyclohexa-2,5-dienylidene)-phenyl-acetonitrile; (4-Trichloroacetoxyimino-cyclohexa-2,5-dienylidene)-phenyl-acetonitrile; (4-Pentafluorobenzoyloxyimino-cyclohexa-2,5-dienylidene)-phenyl-acetonitrile; (4-Triphenylsiloxyimino-cyclohexa-2,5-dienylidene)-phenyl-acetonitrile; (5-Diethoxyphosphoryloxyimino-5H-thiophen-2-ylidene)-(2-methylphenyl)-acetonitrile; (5-Diphenoxyphosphoryloxyimino-5H-thiophen-2-ylidene)-(2-methylphenyl)-acetonitrile; (5-Diethoxythiophosphoryloxyimino-5H-thiophen-2-ylidene)-(2-methylphenyl)-acetonitrile; (5-Trichloroacetoxyimino-5H-thiophen-2-ylidene)-(2-methylphenyl)-acetonitrile; (5-Pentafluorobenzoyloxyimino-5H-thiophen-2-ylidene)-(2-methylphenyl)-acetonitrile; (5-Triphenylsiloxyimino-5-thiopen-2-ylidene)-(2-methylphenyl)-acetonitrile; (5-Diphenoxyphosphoryloxyimino-5H-thiophen-2-ylidene)-(2-methylphenyl)-acetonitrile (4-Diphenoxyphosphoryloxyimino-cyclohexa-2,5-dienylidene)-(4-methylphenyl)-acetonitrile; (4-Diphenoxyphosphoryloxyimino-cyclohexa-2,5-dienylidene)-(4-methylphenyl)-acetonitrile; (4-Diphenoxyphosphoryloxyimino-cyclohexa-2,5-dienylidene)-(3,4-dimethoxyphenyl)-acetonitrile; (4-Diphenoxyphosphoryloxyimino-cyclohexa-2,5-dienylidene)-(4-methltiophenyl)-acetonitrile; (4-Diphenoxyphosphoryloxyimino-cyclohexa-2,5-dienylidene)-(4-dimethylaminophenyl)-acetonitrile; (5-Diphenoxyphosphoryloxyimino-5H-thiophen-2-ylidene)-phenyl-acetonitrile; (5-Diphenoxyphosphoryloxyimino-5H-thiophen-2-ylidene)-(2-chlorophenyl)-acetonitrile; (5-Diphenoxyphosphoryloxyimino-5H-thiophen-2-ylidene)-(4-methoxyphenyl)-acetonitrile; (5-Diphenoxyphosphoryloxyimino-5H-thiophen-2-ylidene)-(4-methoxyphenyl)-acetonitrile; (5-Diphenoxyphosphoryloxyimino-5H-thiophen-2-ylidene)-(4-methylthiophenyl)-acetonitrile; (5-Diphenoxyphosphoryloxyimino-5H-thiophen-2-ylidene)-(4-dimethylaminophenyl)-acetonitrile; (4-Diphenoxyphosphoryloxyimino-3-methylcyclohexa-2,5-dienylidene)-phenyl-acetonitrile; (4-Diphenoxyphosphoryloxyimino-3-methoxycyclohexa-2,5-dienylidene)-phenyl-acetonitrile; Biphenyl-4-yl-(4-diphenoxyphosphoryloxyimino-cyclohexa-2,5-dienylidene)-acetonitrile; (4-Diphenoxyphosphoryloxyimino-cyclohexa-2,5-dienylidene)-naphthalen-1-yl-acetonitrile; (5-Diphenoxyphosphoryloxyimino-5H-thiophen-2-ylidene)-(2,6-dichlorophenyl)-acetonitrile; (5-Diphenoxyphosphoryloxyimino-6-methoxy-5H-pyridin-2-ylidene)-phenyl-acetonitrile; (4-Diphenoxyphosphoryloxyimino-3-phenylcyclohexa-2,5-dienylidene)-phenyl-acetonitrile; (4-Diphenoxyphosphoryloxyimino-4H-naphthalen-1- ylidene)-(4-chlorophenyl)-acetonitrile; (5-Diphenoxyphosphoryloxyimino-1-methyl-1,5-dihydro-pyrrol-2-ylidene)-phenyl-acetonitrile; (4-Diphenoxyphosphoryloxyimino-3-phenylamino-cyclohexa-2,5-dienylidene)-phenyl-acetonitrile; (4-Diphenoxyphosphoryloxyimino-cyclohexa-2,5-dienylidene)-(2,4-dichlorophenyl)-acetonitrile; (5-Bis(2,2,2-trichloroethoxy)phosphoryloxyimino-5H-thiophen-2-ylidene)-(2-methylphenyl)-acetonitrile; (5-(1,2-Phenylenedioxy) phosphoryloxyimino-5H-thiophen-2-ylidene)-(2-methylphenyl)-acetonitrile; (5-(1,2-Ethylenedioxy)phosphoryloxyimino-5H-thiophen-2-ylidene)-(2-methylphenyl)-acetonitrile;

The invention also relates to mixtures of isomeric forms of the compounds of formula I, Ia and II. Oxime derivatives can be present both in the syn (cis, Z) and the anti (trans, E) form or as mixtures of the two geometrical isomers. In addition, the substituted methylidene group $C(R_1)R_2$ can exhibit two (cis and trans) isomers. Depending on $R_4$, $R_5$ and A, this can result in up to four geometrical isomers. In the present invention, both the individual geometrical isomers and any mixtures of two, three or four geometrical isomers can be used.

Oxime derivatives (of formulae I, Ia and II) can be prepared by methods described in the literature, for example by reacting suitable free oximes (of formula IVa and IVb) with a halide compound such as phosphoryl chloride, haloalkynoylchloride etc. (of formula V):

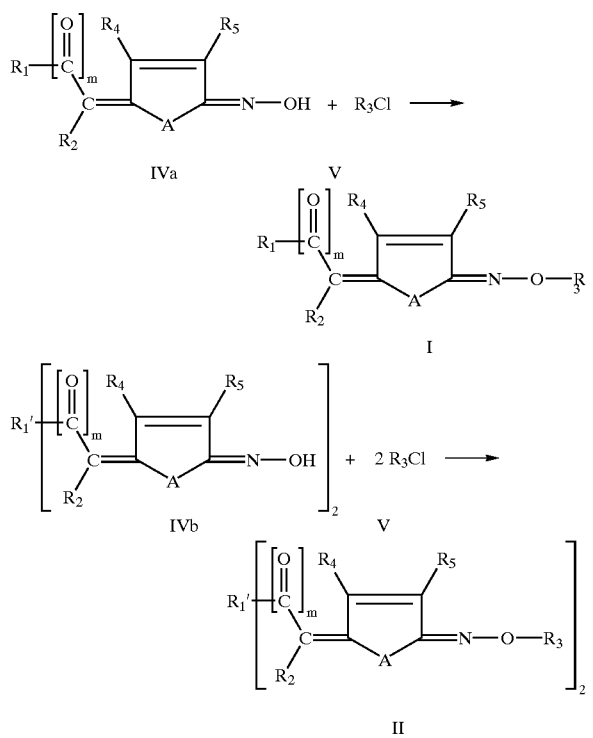

$R_1$, $R'_1$, $R_2$, $R_3$, $R_4$, $R_5$, A and m are as defined above.

These reactions are for example carried out in an inert solvent such as tetrahydrofuran (THF) or dimethylformamide (DMF) in the presence of a base, for example a tertiary amine, such as triethylamine, or by reaction of the salt of an oxime with the appropriate chloride compound such as, for example, phosphoryl chloride. These methods are disclosed, for example, in EP 48615. The sodium salts of oximes can be obtained, for example, by reacting the oxime in question with a sodium alcoholate in DMF.

The oximes of formula IVa required for the reaction can be prepared according to known procedures, for example by reacting benzyl cyanides or cyanomethyl heterocycles with nitrobenzenes or nitronaphtalenes in the presence of a base (such as, for example, sodium methoxide or potassium hydroxide) in a polar solvent such as, for example, methanol or DMF, as described by R. B. Davis, L. C. Pizzini & E. J. Bara, J. Org. Chem. 26, 4270 (1961) or P. Fournary and T. Marey, Bull. Soc. Chim. Fr. 3223 (1968). Temperatures of −80° C. to +80° C., especially −10° C. to 60° C. are suitable for the reaction. Phase transfer catalysis is also suitable to prepare oxime intermediates of formula IVa. K. Takahashi, et al. have described the use of benzyltriethyl ammonium chloride and 50% aqueous sodium hydroxide for the reaction of nitrobenzene with benzyl cyanide (K. Takahashi, T. Tsuboi, K. Yamada, H. Iida, Nippon Kagaku Kaishi 144-7 (1976); Chemical Abstract No. 84:105162). Oximes of formula IVa and IVb have also been prepared as intermediates in the synthesis of various pharmaceutical compounds (e.g. U.S. Pat. No. 5,043,327, U.S. Pat. No. 5,521,187, EP 371564, EP 541153, ES 524551) or for use as UV absorbers (for instance, in U.S. Pat. No. 3,374,248).

Oximes can also be obtained by reacting a suitable carbonyl or thionylcarbonyl compound with hydroxylamine or a hydroxylammonium salt.

The preparation of the chlorides used to introduce the radical $R_3$ is known to the person skilled in the art. Many of these compounds are commercially available.

The invention relates also to the use of compounds of formulae I and II as described above, as photoinitiators for compounds which can be crosslinked under the action of an acid and/or as solubility inhibitors for compounds the solubility of which is altered under the action of an acid.

Accordingly, also a method for crosslinking compounds which can be crosslinked under the action of an acid as well as altering the solubility of compounds whose solubility can be altered under the action of an acid, wherein compounds of formulae I or II are used as photoinitiators is subject of the invention.

In photocrosslinkable compositions, oxime derivatives act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Finally, oxime derivatives which are sparingly soluble in an aqueous-alkaline developer can be rendered soluble in the developer by means of light-induced conversion into the free acid, with the result that they can be used as solubility inhibitors in combination with suitable film-forming resins.

The invention therfore also pertains to a composition comprising
  a) at least one compound which can be crosslinked under the action of an acid and/or
  b) at least one compound the solubility of which is altered under the action of an acid and
  c) as latent acid photoinitiator, at least one compound of formula I or II as described above. These compositions may in addition to component c) comprise further photoinitiators, sensitizers and/or additives.

Resins which can be crosslinked by acid catalysis are, for example, mixtures of polyfunctional alcohols or hydroxygroup-containing acrylic and polyester resins, or partially hydrolysed polyvinylacetals or polyvinyl alcohols with polyfunctional acetal derivatives. Under certain conditions, for example, the acid-catalysed self-condensation of acetal-functionalised resins is also possible.

In addition, oxime derivatives can be used, for example, as hardeners, which can be activated by light, for siloxane group-containing resins. These resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. This type of polycondensation of polysiloxanes is described, for example, in J. J. Lebrun, H. Pode, Comprehensive Polymer Science, Vol. 5, p. 593, Pergamon Press, Oxford, 1989.

It is desirable in the reactions for the acid to be released when irradiated with light of various wavelengths. Surprisingly, it has been found that the new oxime derivatives of formula I, Ia and II are thermally and chemically stable and in addition capable of releasing the acid when irradiated with light. In addition they are bleached after exposure to light, a property which is very helpful for homogeneous generation of the acid throughout the entire thickness of the compositions irradiated by the light and which property is used for the curing of thick layers or the production of colourless articles with visible light.

Oxime derivatives, as already mentioned above, can be used as hardeners, which can be activated by light, for acid-curable resins. Suitable acid-curable resins are all resins the curing of which can be accelerated by acid catalysts, such as aminoplasts or phenolic resole resins. These resins are for example, melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins which are covered by the expression acrylic, polyester and alkyd resins are described, for example, in Wagner, Sarx/Lackkunstharze (Munich, 1971), pages 86 to 123 and 229 to 238, or in Ullmann/Encyclopädie der techn. Chemie, 4th Edition, Volume 15 (1978), pages 613 to 628, or Ullmann's Encyclopedia of Industrial Chemistry, Verlag Chemie, 1991, Vol. 18, 360 ff., Vol. A19, 371 ff.

The composition can for example be used as a surface coating.

The surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. As already mentioned above, for example polysiloxanes can also be crosslinked using acid catalysis. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxy-methyl-3,4-dihydro-2H-pyran; vinyl esters, such as vinyl acetate and vinyl stearate, mono- and di-olefins, such as a-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula I, Ia or II. In this connection a) radical polymerisation initiators or b) photoinitiators can additionally be used. The former initiate polymerisation of the unsaturated groups during heat treatment, the latter during UV irradiation.

According to the invention, the compositions, which can be activated by light, may comprise further photoinitiators, sensitisers and/or additives in addition to component c), or the compounds of formula I or II can be used together with further photoinitiators, sensitisers and/or additives.

Examples of additional photoinitiators are radical photoinitiators, such as those from the class of the benzophenones, acetophenone derivatives, such as α-hydroxycycloalkylphenyl ketone, dialkoxyacetophenone, α-hydroxy- or α-amino-acetophenone, 4-aroyl-1,3-dioxolans, benzoin alkyl ethers and benzil ketals, monoacylphosphine oxides, bisacylphosphine oxides, camphor quinone, phenylglyoxalic esters and derivatives thereof, dimeric phenylglyoxalic esters, peresters, e.g. benzophenone tetracarboxylic peresters as described for example in EP 126541, ferrocenium compounds, or titanocenes, e.g. bis(cyclopentadienyl)-bis(2,6-di-fluoro-3-pyrryl-phenyl) titanium. Examples of especially suitable additional photoinitiators are: 1-(4-dodecylbenzoyl)-1-hydroxy-1-methyl-ethane, 1-(4-isopropylbenzoyl)-1-hydroxy-1-metyl-ethane, 1-benzoyl-1-hydroxy-1-methyl-ethane, 1-[4-(2-hydroxyethoxy)-benzoyl]-1-hydroxy-1-methyl-ethane, 1-[4-(acryloyloxyethoxy)-benzoyl]-1-hydroxy-1-methyl-ethane, diphenyl ketone, phenyl-1-hydroxy-cyclohexyl ketone, (4-morpholinobenzoyl)-1-benzyl-1-dimethylamino-propane, 1-(3,4-dimethoxyphenyl)-2-benzyl-2-dimethylamino-butan-1-one, (4-methylthioben-zoyl)-1-methyl-1-morpholino-ethane, benzil dimethyl ketal, bis (cyclopentadienyl)-bis(2,6-di-fluoro-3-pyrryl-phenyl) titanium, trimethylbenzoyldiphenylphosphine oxide, bis(2, 6-dimethoxy-benzoyl)-(2,4,4-trimethyl-pentyl)-phosphine oxide, bis(2,4,6-trimethylbenzoyl)-2,4-dipentyloxyphenyl-phosphine oxide or bis(2,4,6-trimethylbenzoyl)phenyl-phosphine oxide. Further suitable additional photoinitiators are to be found in U.S. Pat. No. 4,950,581, column 20, line 35 to column 21, line 35. Other examples are trihalomethyltriazine derivatives or hexaarylbisimidazolyl compounds, e.g. 2-[2-(4-methoxy-phenyl)-vinyl]-4,6-bis-trichloromethyl-[1,3,5]-triazine, 2-(4-methoxy-phenyl)-4,6-bis-trichloromethyl-[1,3,5]-triazine, 2-(3,4-dimethoxy-phenyl)-4,6-bis-trichloromethyl-[1,3,5]-triazine, 2-methyl-4,6-bis-trichloromethyl-[1,3,5]-triazine, hexaarylbisimidazole/coinitiators systems, e.g. ortho-chlorohexaphenyl-bisimidazole combined with 2-mercaptobenzthiazole. Further examples for additional photoinitiators are borate compounds, as for example described in U.S. Pat. No. 4,772,530, EP 775706, GB 2307474, GB 2307473 and GB 2304472. The borate compounds preferably are used in combination with electron acceptor compounds, such as, for example dye cations, or thioxanthone derivatives.

Further examples of additional photoinitiators are peroxide compounds, e.g. benzoyl peroxide (other suitable peroxides are described in US Patent 4 950 581, column 19, lines 17–25) or cationic photoinitiators, such as aromatic sulfonium or iodonium salts, for example such as disclosed in U.S. Pat. No. 4,950,581, column 18, line 60 to column 19, line 10, or cyclopentadienyl-arene-iron(II) complex salts, for example ($\eta^6$-isopropylbenzene)($\eta^5$-cyclopentadienyl)-iron(II) hexafluorophosphate. Further examples of additional photoinitiators are O-acyloxime esters, for example 1-phenyl-1,2-propanedione-2-O-ethoxycarbonyl oxime.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers.

UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of these compounds can be used with or without the addition of sterically hindered amines (HALS).

Examples of such UV absorbers and light stabilisers are
1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-($\alpha$,$\alpha$-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$— where R=3'-tert-butyl-4'-hydroxy-5'-2H-benzotriazol-2-ylphenyl, 2-[2'-hydroxy-3'-($\alpha$,$\alpha$-dimethylbenzyl)-5'-(1,1,3,3-tetramethylbutyl)-phenyl]benzotriazole; 2-[2'-hydroxy-3'-(1,1,3,3-tetramethylbutyl)-5'-($\alpha$,$\alpha$-dimethylbenzyl)-phenyl]benzotriazole.

2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl $\alpha$-cyano-$\beta$,$\beta$-diphenylacrylate, isooctyl $\alpha$-cyano-$\beta$,$\beta$-diphenylacrylate, methyl $\alpha$-carbomethoxycinnamate, methyl $\alpha$-cyano-$\beta$-methyl-p-methoxy-cinnmate, butyl $\alpha$-cyano-$\beta$-methyl-p-methoxy-cinnamate, methyl $\alpha$-carbomethoxy-p-methoxycinnamate and N-($\beta$-carbomethoxy-$\beta$-cyanovinyl)-2-methylindoline.

5. Sterically hindered amines, for example bis(2,2,6,6-tetramethyl-4-piperidyl)sebacate, bis(2,2,6,6-tetramethyl-4-piperidyl)sebacate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N, N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

6. Oxamides, for example 4,4'-dioctyloxyoxanilide, 2,2'-diethoxyoxanilide, 2,2'-dioctyioxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyt)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[4-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz-[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the composition, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP 738928, EP 22188), keto-coumarines (as described e.g. in U.S. Pat. No. 5,534,633, EP 538997, JP 8272095-A), styryl -coumarines (as described e.g. in EP 624580), 3-(aroylmethylene)-thiazolines, thioxanthones, condensed aromatic compounds, such as perylene, aromatic amines (as described, for example, in U.S. Pat. No. 4,069,954 or WO 96/41237) or cationic and basic colourants (as described, for example, in U.S. Pat. No. 4,026,705), for example eosine, rhodanine and erythrosine. colourants, as well as dyes and pigments as described for example in JP 8320551-A, EP 747771, JP 7036179-A, EP 619520, JP 6161109-A, JP 6043641, JP 6035198-A, WO 93/15440, EP 568993, JP 5005005-A, JP 5027432-A, JP 5301910-A, JP 4014083-A, JP 4294148-A, EP 359431, EP 103294, U.S. Pat. No. 4,282,309, EP 39025, EP 5274, EP 727713, EP 726497 or DE 2027467.

Other customary additives are—depending on the intended use—optical brighteners, fillers, pigments, colourants, wetting agents or flow improvers.

For curing thick and pigmented coatings, the addition of micro glass beads or powdered glass fibres, as described in U.S. Pat. No. 5,013,768, is suitable.

The choice of additive is made depending on the field of application and on properties required for this field. The additives described above are customary in the art and accordingly are added in amounts which are usual in the respective application.

Oxime derivatives can also be used, for example, in hybrid systems. These systems are based on formulations that are fully cured by two different reaction mechanisms. Examples thereof are systems which comprise components which are capable of undergoing an acidcatalysed crosslinking reaction or polymerisation reaction, but which also comprise further components which crosslink by a second mechanism. Examples of the second mechanism are, for example, radical full cure, oxidative crosslinking or humidity-initiated crosslinking. The second curing mechanism may be initiated purely thermally, if necessary with a suitable catalyst, or also by means of light using a second photoinitiator.

If the composition comprises a radically crosslinkable component, the curing process, especially of compositions which are pigmented (for example with titanium dioxide), can also be assisted by the addition of a component which is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP 245639. The addition of redox initiators, such as cobalt salts, enables the curing to be assisted by oxidative crosslinking with oxygen from the air.

The surface coating can be applied by one of the methods customary in the art, for example by spraying, painting on or immersion. When suitable surface coatings are used, electrical application, for example by electroimmersion coating, is also possible. After drying, the surface coating film is irradiated. If necessary, the surface coating film is then fully cured by means of heat treatment.

The compounds of formulae I or II can also be used for curing mouldings made from composites. A composite consists of a self-supporting matrix material, for example a glass fibre fabric, impregnated with the photocuring formulation.

Resist systems can be prepared by image-wise irradiation of systems comprising compounds of formulae I or II, followed by a developing step. As already mentioned above, compounds of formulae I or II can be used as photosensitive acid donors in a photoresist.

The invention accordingly relates also to a photoresist based on oxime compounds as photosensitive acid donors, the photoresist comprising as oxime compound a compound of formulae I or II.

The difference in solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive. If, on the other hand, these components reduce the solubility of the composition after irradiation, the resist is negative.

The invention accordingly relates also to a negative photoresist and to a positive photoresist.

The oxime derivatives of formulae I or II can also be used in chemically amplified resists. A chemically amplified photoresist is understood to be a resist composition the photosensitive component of which, when irradiated, provides only that amount of acid which is required to catalyse a chemical reaction of at least one acid-sensitive component of the resist, as a result of which the ultimate differences in solubility between irradiated and non-irradiated areas of the photoresist first develop.

The invention accordingly relates also to a chemically amplified photoresist.

Subject of the invention further is the use of a compound of the formula I or II as photosensitive acid donor in a photoresist.

Such resists exhibit an outstanding lithographic sensitivity to radiation of different wavelengths, since compounds of formulae I or II can be easily tuned over a broad range of the electromagnetic spectrum. The photoresists according to the invention have excellent lithographic properties, especially a high sensitivity, and homogeneous exposure-conditions over the whole resist thickness due to the fact that the optical absorption is bleached upon irradiation.

Acid-sensitive components that produce a negative resist characteristic are especially compounds which, when catalysed by acid (the acid formed during irradiation of the compounds of formulae I or II), are capable of undergoing a crosslinking reaction with themselves and/or with one or more further components of the composition. Compounds of this type are, for example, the known acid-curable resins, such as, for example, acrylic, polyester, alkyd, melamine, urea, epoxy and phenolic resins or mixtures thereof. Amino resins, phenolic resins and epoxy resins are very suitable. Acid-curable resins of that type are generally known and are described, for example, in Ullmann's Encyclopädie der technischen Chemie, 4th Edition, Vol. 15 (1978), p. 613–628. The crosslinker components should generally be present in a concentration of from 2 to 40, preferably from 5 to 30, percent by weight, based on the total solids content of the negative composition.

Especially preferred as acid-curable resins are amino resins, such as non-etherified or etherified melamine, urea, guanidine or biuret resins, especially methylated melamine resins or butylated melamine resins, corresponding glycolurils and urones. Resins in this context are to be understood by both, customary technical mixtures, which generally also comprise oligomers, and pure and high purity compounds. N-Methoxymethyl melamine and tetramethoxymethyl glucoril and N,N'-dimethoxymethylurone are the acid-curable resins given the greatest preference.

The concentration of the compounds of formula I or II in negative resists is in general from 0.1 to 30, preferably up to 20, percent by weight, likewise based on the total solids content of the compositions. From 1 to 15 percent by weight is especially preferred.

Where appropriate, the negative photoresist compositions may additionally comprise a film-forming polymeric binder. This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tertbutylphenol, p-nonylphenol, p-phenylphenol, resorcinol, bis(4-hydroxyphenyl)methane or 2,2-bis(4-hydroxyphenyl) propane. Also suitable are homo- and co-polymers based on ethylenically unsaturated phenols, for example homopolymers of vinyl- and 1-propenyl-substituted phenols, such as p-vinylphenol or p-(1-propenyl)phenol or copolymers of these phenols with one or more ethylenically unsaturated materials, for example styrenes. The amount of binder should generally be from 30 to 99 percent by weight, e.g. 30 to 95 percent by weight or 40 to 80 percent by weight, preferably, from 40 to 95 percent by weight.

The invention thus includes, as a special embodiment, as already mentioned above, negative, alkali-developable photoresists, comprising an oxime derivative of formula I or II as described above, an alkali-soluble phenolic resin as binder and a component which, when catalysed by an acid, undergoes a crosslinking reaction with itself and/or with the binder.

An especially preferred form of this negative resist comprises from 1 to 15 percent by weight of an oxime derivative of formula I or II, from 40 to 99 percent by weight, e.g. 40 to 95 percent by weight, of a phenolic resin as binder, for example one of those mentioned above, and from 0.5 to 30 percent by weight of a melamine resin as crosslinking agent, the percentages relating to the solids content of the composition. With novolak or especially with polyvinyl phenol as binder, a negative resist having especially good properties is obtained.

Oxime derivatives of formula I or II can also be used as acid generators, which can be activated photochemically, for the acid-catalysed crosslinking of, for example, poly (glycidyl)methacrylates in negative resist systems. Such crosslinking reactions are described, for example, by Chae et al. in Pollimo 1993, 17(3), 292.

Monomeric or polymeric compounds that are alkali-insoluble but are cleaved in the presence of acid, or are capable of being rearranged intramolecularly, in such a manner that reaction products remain which are soluble in a customary alkaline developer and/or which cause an otherwise alkali-insoluble and acid-resistant additional binder to become soluble in the developer, produce a positive characteristic in photoresist compositions according to the invention. Substances of this type are referred to hereinafter as solution inhibitors.

As already indicated hereinbefore, the invention therefore includes, as a further special embodiment, positive alkaline-developable photoresists, comprising a compound of formula I or II and at least one compound that substantially prevents the composition from dissolving in an alkaline developer, but which can be cleaved in the presence of an acid in such a manner that reaction products remain which are soluble in the developer and/or which cause an acid-resistant additional binder that would otherwise be virtually insoluble in the developer to dissolve in the developer.

There may be used as solution inhibitors monomeric and polymeric organic compounds having functional groups which would be soluble per se in an alkaline medium, for example aromatic hydroxy groups, carboxylic acid groups, secondary amino groups and keto or aldehyde groups, but which have been chemically so altered by reaction with a suitable compound that they are insoluble in aqueous alkali, the protecting groups formed in the mentioned reaction being capable of being cleaved again by acid catalysis in such a manner that the functional groups are recovered in their original form.

For the protection of hydroxy groups, carboxylic acid groups or secondary amino groups there are suitable, for example;, dihydrofuran or 3,4-dihydropyran and the derivatives thereof, benzyl halides, alkyl halides, haloacetic acid, haloacetic acid esters, chlorocarbonic acid esters, alkylsulfonyl halides, aromatic sulfonyl halides, dialkyl dicarbonates or trialkylsilyl halides, it being possible for the reactions to form the protected derivatives to be carried out in known manner. Customary conversion into ketals and acetals is suitable for protecting keto and aldehyde groups.

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

In positive resists of the mentioned type a film-forming, polymeric solution inhibitor can either be the only binder in the photoresist or can be used in admixture with an acid-inert binder and, where appropriate, a monomeric solution inhibitor.

Examples of acid-inert binders are novolaks, especially those based on o-, m- or p-cresol and formaldehyde, also poly(p-hydroxystyrene), poly(p-hydroxy-a-methylstyrene) and copolymers of p-hydroxystyrene, p-hydroxy-a-methylstyrene and acetoxystyrene.

Examples of polymeric solution inhibitors are novolaks, especially those based on o-, m- or p-cresol and formaldehyde, poly(p-hydroxystyrene), poly(p-hydroxy-a-methylstyrene), copolymers of p-hydroxystyrene or p-hydroxy-a-methylstyrene and acetoxystyrene or acrylic acid and/or methacrylic acid and (meth)acrylic acid esters, which are reacted in a known manner with dihydrofuran, 3,4-dihydropyran, benzyl halides, alkyl halides, haloacetic acid, haloacetic acid esters, chlorocarbonic acid esters, alkylsulfonyl halides, aromatic sulfonyl halides, dialkyl dicarbonate or trialkylsilyl halides. Also suitable are polymers of p-(2-tetrahydropyranyl)-oxystyrene or p-(tert-butyloxycarbonyl)-oxystyrene with (meth)acrylic acid, (meth)acrylic acid esters and/or p-acetoxystyrene and polymers of p-hydroxystyrene and/or p-(2-tetrahydropyranyl)-oxystyrene with 3-hydroxybenzyl (meth)acrylates, which can, if necessary, additionally be protected by reaction with one of the compounds listed above.

Especially suitable are polymers that are—depending on the light sources used for irradiation —transparent in the wavelength range used for irradiation. Wavelengths can vary between 180 and 1500 nm. The polymers can carry both, groups that, after acid-catalysed deprotecting, bring about a change in solubility, and hydrophobic and hydrophilic groups that increase the solubility of the acid generator and ensure aqueous-alkaline developability. Examples of such polymers are acrylates and methacrylates prepared by co-, ter-, or quater-polymerisation from the corresponding monomers like methyl (meth)acrylate, (meth)acrylic acid, tert-butyl (meth)acrylate, 3-oxocyclohexyl (meth)acrylate, tetrahydropyranyl (meth)acrylate, adamantyl (meth)acrylate, cyclohexyl (meth)acrylate, norbornyl (meth)acrylate. The monomers can also combine two of the above mentioned structures like for example (2-tetrahydropyranyl) oxynorbonylalcohol acrylates or (2-tetrahydropyranyl) oxymethyltricyclododecanemethanol methacrylates. Examples for such monomers are given in U.S. Pat. No. 5,621,019. The monomers may also carry organosilicon radicals in order, for example, to further increase the resistance in the case of dry etching processes, like for example trimethylsilylmethyl (meth)acrylate.

The invention accordingly also relates to a chemically amplified positive resist comprising as photosensitive acid donor a compound of formula I or II.

The invention further relates also to a photoresist comprising polymers that are transparent down to the wavelength region of 180 nm.

A special embodiment of the positive resist according to the invention comprises from 75 to 99.5 percent by weight of a film-forming polymer that contains protecting groups which can be removed by acid catalysis, and from 0.5 to 25 percent by weight of oxime derivatives of formula I or II, the percentages being based on the solids content of the compositions. In this context, preference is given to compositions comprising from 80 to 99 percent by weight of the mentioned polymer and from 1 to 20 percent by weight of the oxime derivatives.

Another embodiment is a positive resist comprising from 40 to 90 percent by weight of an acid-inert film-forming polymer as binder, from 5 to 40 percent by weight of a monomeric or polymeric compound having protecting groups removable by acid catalysis and from 0.5 to 25 percent by weight of oxirne derivatives of formula I or II, the percentages relating to the solids content of the compositions. Of these compositions, preference is given to those comprising from 50 to 85 percent by weight of acid-inert binder, from 10 to 30 percent by weight of monomeric or polymeric solution inhibitor and from 1 to 20 percent by weight, e.g. from 1 to 15 percent by weight of oxime derivatives.

Oxime derivatives of formula I or II can also be used as solubility enhancers, which can be activated by light. In this case, the compounds are added to a film-forming material which does not comprise any components which polymerise with the oxime derivatives when heated or when irradiated with actinic radiation. However, the oxime derivatives reduce the speed at which the film-forming material dissolves in a suitable developer medium. This inhibiting effect can be cancelled by irradiating the mixture with actinic radiation, so that a positive image can be produced. This application is described, for example, in EP 241423.

A further special embodiment of the invention is, finally, a positive resist comprising a compound of formula I or II and a binder which is virtually insoluble in an alkaline developer and which becomes soluble in the developer in the presence of the photolysis products of the compound of formula I or II. In this case the amount of the mentioned oxime derivative compound is generally from 5 to 50 percent by weight, based on the solids content of the composition.

The use of the oxime derivatives according to the invention in chemically amplified systems, which operates on the principle of the removal of a protecting group from a polymer, generally produces a positive resist. Positive resists are preferred to negative resists in many applications, especially because of their greater resolution. There is, however, also interest in producing a negative image using the positive resist mechanism, in order to combine the advantages of the high degree of resolution of the positive resist with the properties of the negative resist. This can be achieved by introducing a so-called image-reversal step as described, for example, in EP 361906. For this purpose, the image-wise irradiated resist material is treated, before the developing step, with, for example, a gaseous base, whereby the acid which has been produced image-wise is neutralised. Then, a second irradiation, over the whole area, and thermal after treatment are carried out and the negative image is then developed in the customary manner.

In addition to the mentioned constituents, both the negative and the positive photoresist compositions may additionally comprise one or more of the additives customarily used in photoresists in the amounts familiar to a person skilled in the art. Examples are flow improvers, wetting agents, adhesives, thixotropic agents, colourants, pigments, fillers, solubility accelerators and so on. The reaction can be accelerated by the addition of photosensitisers which shift and/or broaden the spectral sensitivity. These are especially aromatic carbonyl compounds, such as benzophenone, thioxanthone, anthraquinone and 3-acylcoumarin derivatives and also 3-(aroylmethylene) thiazolines, but also eosine, rhodanine and erythrosine colourants.

Other compounds that accelerate the acid formation or enhance the acid concentration may also be used in combination: with the oxime derivatives of the formulae I or II according to the invention in positive or negative resists or imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

For application, the compositions must generally also comprise a solvent. Examples of suitable solvents are ethyl acetate, 3-methoxymethyl propionate, ethyl pyruvate, 2-heptanone, diethyl glycol dimethyl ether., cyclopentanone, cyclohexanone, γ-butyrolactone, ethyl methyl ketone, 2-ethoxyethanol, 2-ethoxyethyl acetate and especially 1-methoxy-2-propyl acetate.

The solvent may also be a mixture, for example of two or more of the above-mentioned solvents. The choice of solvent and the concentration of the solvent depend, for example, on the nature of the composition and on the coating method.

The solution usually is uniformly applied to a substrate by means of known coating methods, for example by spin-coating, immersion, knife coating, curtain pouring techniques, brush application, spraying and reverse roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.01 μm to more than 100 μm.

Possible areas of use of the composition according to the invention are as follows: use as photoresists for electronics, such as etching resists, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques. The coating substrates and processing conditions vary accordingly.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

After the coating operation, the solvent is generally removed by heating, resulting in a layer of the photoresist on the substrate. The drying temperature must of course be lower than the temperature at which certain components of the resist might be thermally cured. Care must be taken in this respect especially in the case of negative photoresists. In general, drying temperatures should not exceed from 80 to 130° C.

The resist coating is then irradiated image-wise. The expression "image-wise irradiation" includes irradiation in a predetermined pattern using actinic radiation, i.e. both irradiation through a mask containing a predetermined pattern, for example a transparency, and irradiation using a laser beam which is moved over the surface of the coated substrate, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 p 275–281 and by K. P. Nicolay in Offset Printing 1997, 6, p 34–37.

After the irradiation and, if necessary, thermal treatment, the unirradiated sites (in the case of positive resists) or the irradiated sites (in the case of negative resists) of the composition are removed in a manner known per se using a developer.

It is generally necessary to allow a certain period of time prior to the developing step in order to allow the acid-sensitive components of the resist composition to react. In order to accelerate this reaction and hence the development of a sufficient difference in solubility between the irradiated and unirradiated sections of the resist coating in the developer, the coating is preferably heated before being developed. The heating can also be carried out or begun during the irradiation. Temperatures from 60 to 150° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under these processing conditions.

The coating is then developed, the portions of the coating which, after irradiation, are more soluble in the developer being removed. If necessary, slight agitation of the workpiece, gentle brushing of the coating in the developer bath or spray developing can accelerate this process step. For example the aqueous-alkaline developers customary in resist technology may be used for developing. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5N, but are usually diluted in suitable manner before use. For example solutions having a normality of approximately 0.1 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve®/water.

Subject of the invention is a process for the preparation of a photoresist, by

A process for the preparation of a photoresist, by
(1) applying to a substrate a composition as described above;
(2) optionally heating to remove a solvent from the composition:
(3) image-wise irradiating with light of wavelengths between 150 and 1500 nm;
(4) thermally treating the irradiated composition; and
(5) removing the non-cured areas by development and thus achieving a patterned coating.

It is known from EP 592139 that oxime derivatives can be used as acid generators, which can be activated by light in compositions that are suitable for the surface treatment and cleaning of glass, aluminum and steel surfaces. The use of these compounds in such organosilane systems results in compositions that have significantly better storage stability than those obtained when the free acid is used.

Oxime derivatives can also be used to produce so-called "print-out" images when the compound is used together with a colourant that changes colour when the pH changes, as described e.g. in JP Hei 4 328552-A or in U.S. Pat. No. 5,237,059. Such colour-change systems can be used according to EP 199672 also to monitor goods that are sensitive to heat or radiation. In addition the newly claimed compounds of formula I or II exhibit already a colour change on their own when they are exposed to light of suitable wavelength. This color-change must not be as pronounced as in the case of using it in combination with the beforementioned acid-sensitive colourants, but it is well visible.

In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with oxime derivatives can be used as light indicators or simple throw away dosimeters. Especially for light, that is invisible to the human eye, like UV- or IR-light, such dosimeters are of interest.

The oxime derivatives of the present invention can also be used to shape polymers that undergo an acid induced transition into a state where they have the required properties using photolithography. For instance the oxime derivatives can be used to pattern conjugated emissive polymers as described in M. L. Renak; C. Bazan; D. Roitman; Advanced materials 1997, 9, 392. Such patternd emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coating, insulating layers and buffer layers in the production of microchips and printed circuit boards.

The formulations may also be used as conformal coatings, photoimagable dielectricas as they are used in sequential build up systems for printed circuit boards, stress buffer layers and isolation layers in the manufacturing of computer chips.

It is known that conjugated polymers like, e.g. polyanilines can be converted from semiconductive to conductive state by means of proton doping. The oxime derivatives of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable for the crosslinking of compositions comprising compounds of formula I or II are radiation sources that emit radiation of a wavelength of approximately from 150 to 1500, for example from 180 to 1000 or preferably from 240 to 700 nanometers. Both point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the lamp and the substrate according to the invention to be irradiated can vary, for example, from 2 cm to 150 cm, according to the intended use and the type and/or strength of the lamp. Suitable light sources are therefore especially mercury vapour lamps, in particular medium and high pressure mercury lamps. From the radiation of these lamps emission lines at other wavelengths can, if desired, be filtered out. This is especially the case for relatively short wavelength radiation. It is, however, also possible to use low energy lamps (for example fluorescent tubes) that are capable of emitting in the appropriate wavelength range. An example thereof is the Philips TL03 lamp. Another type of light source that can be used are the light emitting diodes (LED) that emit at different wavelengths throughout the whole spectrum either as small band emitting source or as broad band (white light) source. Also suitable are laser light sources, for example excimer lasers, such as Kr-F lasers for irradiation at 248 nm, Ar-F lasers at 193 nm, or $F_2$ lasers at 157 nm. Lasers in the visible range and in the infrared range can also be used. Very especially suitable is radiation of the mercury h and g lines at wavelengths of 436 and 405 nanometers. A suitable laser-beam source is, for example, the argon-ion laser, which emits radiation at wavelengths of 454, 458, 466, 472, 478, 488 and 514 nanometers.

Nd-YAG-lasers emitting light at 1064 nm and it's second and third harmonic (532 nm and 355 nm respectively) can also be used. Also suitable is, for example, a helium/cadmium laser having an emission at 442 nm or lasers that emit in the UV range. With this type of irradiation, it is not absolutely essential to use a photomask in contact with the photopolymeric coating to produce a positive or negative resist; the controlled laser beam is capable of writing directly onto the coating. For this purpose the high sensitivity of the materials according to the invention is very advantageous, allowing high writing speeds at relatively low intensities. On irradiation, the oxime derivative in the composition in the irradiated sections of the surface coating decomposes to form acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures. The surface coating to be cured can be exposed directly to sunlight or daylight-equivalent light sources. The curing can, however, also take place behind a transparent layer (e.g. a pane of glass or a sheet of plastics).

The compounds of formulae I or II are generally added to the compositions in an amount from 0.1 to 30% by weight, for example from 0.5 to 10% by weight, especially from 1 to 5% by weight.

Subject of the invention is a method of crosslinking compounds which can be crosslinked under the action of an acid, which method comprises adding a compound of formula I and/or II according to claim 1 to the above-mentioned compounds and irradiating imagewise or over the whole area with light having a wavelength of 180–1500 nm.

The invention relates also to the use of compounds of formulae I or II as photosensitive acid donors in the preparation of surface coatings, printing inks, printing plates, dental compositions, colour filters, resist materials or image-recording materials, or image-recording materials for recording holographic images, as well as to a method for the preparation of surface coatings, printing inks, printing plates, dental compositions, colour filters, resist materials and as image-recording material, or image-recording material for recording holographic images, which comprises irradiating a composition according to the invention with light having a wavelength of 180–1500 nm. The invention further pertains to the use of a composition as described above and to a method for the preparation of surface coatings, printing inks, printing plates, dental compositions, colour filters, resist materials and as image-recording material, or image-recording material for recording holographic images.

The examples which follow illustrate the invention in more detail. Parts and percentages, as in the remainder of the description and in the claims, are by weight unless indicated otherwise.

EXAMPLE 1

(4-Diethoxyphosphoryloxyimino-cyclohexa-2,5-dienylidene)-phenyl-acetonitrile 1.1: (4-Hydroxyimino-cyclohexa-2,5-dienylidene)-phenyl-acetonitrile 60 g of KOH are dissolved in 300 ml of methanol and heated up to 55° C. To the solution are added 32.2 g (0.27 mol) of phenylacetonitrile followed by 30.8 g (0.25 mol) of nitrobenzene. The reaction mixture is stirred at 55° C. for 4 h. After cooling, 400 ml of water are added with stirring. The resulting solution is acidified by addition of 110 ml of acetic acid in 100 ml of water, leading to a yellow-orange precipitate. The mixture is then filtered, and the yellow solid is washed with a mixture of methanol and water. The crude product is dried in air, boiled with 150 ml of benzene for 15 min., cooled, filtered and dried under vacuum. 42.6 g (77%) of (4-hydroxyimino-cyclohexa-2,5-dienylidene)-phenyl-acetonitrile are obtained in the form of a yellow solid, having a melting point (mp) of 159–163° C. (dec.). The structure is confirmed by the $^1$H-NMR spectrum (CDCl$_3$), δ [ppm]: 6.75(Z)/6.89(E) (dd, 1H), 7.08(Z)/7.15(E) (dd, 1H), 7.25–7.53 (m, 7H), 9.56 (br s, 1H). $^1$H-NMR reveals that the product is a 50:50 mixture of Z and E isomers. The signals are tentatively assigned to Z and E isomers. 1.2: (4-Diethoxyphosphoryloxyimino-cyclohexa-2,5-dienylidene)-phenyl-acetonitrile 8 g (36 mmol) of (4-hydroxyimino-cyclohexa-2,5-dienylidene)-phenyl-acetonitrile are dissolved in 90 ml of tetrahydrofuran (THF) and cooled in an ice bath. After adding 6.8 g (39 mmol) of diethylphosphoryl chloride to the solution, 5.4 g (54 mmol) of triethylamine are added dropwise, keeping the temperature below 5° C. The reaction mixture is gradually warmed to room temperature, and stirred for 1 h. The reaction mixture is poured into 100 ml of water, and extracted with ethyl acetate. The organic phase is washed with 0.1 N hydrochloric acid solution, water, and sodium chloride solution. The organic phase is dried over MgSO$_4$, the solvent is distilled off, and the residue is purified by flash chromatography on silica gel with ethyl acetate—hexane (1:1) as eluent. The product is a brown liquid. The structure is confirmed by the $^1$H-NMR spectrum (CDCl$_3$); δ [ppm]: 1.37–1.44 (m, 6H), 4.23–4.36 (m, 4H), 6.84(Z)/6.97(E) (dd, 1H), 7.17(Z)/7.21(E) (dd, 1H), 7.26(E)/7.38(Z) (dd, 1H), 7.46–7.55 (m, 6H). $^1$H-NMR reveals that the product is a 67:33 mixture of Z and E isomers. The signals are tentatively assigned to Z and E isomers.

EXAMPLE 2

(4-Diphenoxyphosphoryloxyimino-cyclohexa-2,5-dienylidene)-phenyl-acetonitrile 8 g (36 mmol) of (4-Hydroxyimino-cyclohexa-2,5-dienylidene)-phenyl-acetonitrile, prepared as described in Example 1.1, are dissolved in 90 ml of tetrahydrofuran (THF) and cooled in an ice bath. After adding 10.6 g (39 mmol) of diphenylphosphoryl chloride to the solution, 5.4 g (54 mmol) of triethylamine are added dropwise, keeping the temperature below 5° C. The reaction mixture is gradually warmed to room temperature, and stirred for 1 h. The recation mixture is poured into 100 ml of water, and extracted with ethyl acetate. The organic phase is washed with 0.1N hydrochloric acid solution, water, and sodium chloride solution. The organic phase is dried over $MgSO_4$, the solvent is distilled off, and the residue is purified by flash chromatography on silica gel with ethyl acetate—hexane (1:3) as eluent. The product is a yellow solid with a mp of 100–101° C. The structure is confirmed by the $^1$H-NMR spectrum ($CDCl_3$); δ [ppm]: 6.88 (dd, 1H), 7.18–7.41 (m, 12H), 7.46–7.58 (m, 6H).

EXAMPLE 3

(4-Diethoxythiophosphoryloxyimino-cyclohexa-2,5-dienylidene)-phenyl-acetonitrile 8 g (36 mmol) of (4-Hydroxyimino-cyclohexa-2,5-dienylidene)-phenyl-acetonitrile, prepared as described in example 1.1, are dissolved in 90 ml of tetrahydrofuran (THF) and cooled in an ice bath. After adding 7.5 g (39 mmol) of diethyl chlorothiophosphate to the solution, 5.4 g (54 mmol) of triethylamine are added dropwise, keeping the temperature below 5° C. The reaction mixture is gradually warmed to room temperature, and stirred overnight. The reaction mixture is poured into 100 ml of water, and extracted with ethyl acetate. The organic phase is washed with 0.1N hydrochloric acid solution, water, and sodium chloride solution. The organic phase is dried over $MgSO_4$, the solvent is distilled off, and the residue is purified by flash chromatography on silica gel with ethyl acetate—hexane (1:3) as eluent. The product is a yellow solid, with mp 66–82° C. The structure is confirmed by the $^1$H-NMR spectrum ($CDCl_3$); δ [ppm]: 1.32–1.42 (m, 6H), 4.21–4.37 (m, 4H), 6.87(Z)/6.98(E) (dd, 1H), 7.17(Z)/-7.19(E) (dd, 1H), 7.26(E)17.37(Z) (dd, 1H), 7.43–7.54 (m, 6H). $^1$H-NMR reveals that the product is a 56:44 mixture of Z and E isomers. The signals are tentatively assigned to Z and E isomers.

EXAMPLE 4

(4-Pentafluorobenzoyloxyimino-cyclohexa-2,5-dienylidene)-phenyl-acetonitrile 8 g (36 mmol) of (4-Hydroxyimino-cyclohexa-2,5-dienylidene)-phenyl-acetonitrile, prepared as described in example 1.1, are dissolved in 90 ml of tetrahydrofuran (THF) and cooled in an ice bath. After adding 8.4 g (39 mmol) of pentafluorobenzoyl chloride to the solution, 5.4 g (54 mmol) of triethylamine are added dropwise, keeping the temperature below 5° C. The reaction mixture is stirred at 5° C. for 40 min and then is poured into 200 ml of water. The solid is isolated by filtration. The crude product is purified by recrystallization from 1,2-dichloroethane to afford yellow crystals, having a mp of 202–203° C. (Dec). The structure is confirmed by the $^1$H-NMR spectrum ($CDCl_3$). δ [ppm]: 6.98 (dd, 1H), 7.28 (dd, 1H), 7.36 (dd, 1H), 7.51 (s, 5H), 7.61 (dd, 1 H). $^1$H-NMR reveals the presence of a single isomer.

EXAMPLE 5

(4-Trichloroacetoxyimino-cyclohexa-2,5-dienylidene)-phenyl-acetonitrile 8 g (36 mmol) of (4-Hydroxyimino-cyclohexa-2,5-dienylidene)-phenyl-acetonitrile, prepared as described in example 1.1, are dissolved in 90 ml of tetrahydrofuran (THF) and cooled in an ice bath. After adding 7.2 g (39 mmol) of trichloroacetyl chloride to the solution, 5.4 g (54 mmol) of triethylamine are added dropwise, keeping the temperature below 5° C. While the reaction mixture is stirred at 5° C. for 50 min, a precipitate is formed. The precipitate is filtered off and washed with THF. The filtrate is concentrated by a rotary evaporator. The residue is diluted with 2-propanol (2-PrOH) and stirred at room temperature overnight. After cooling the mixture in an ice bath, the solid is isolated by filtration and washed with 2-PrOH. The product is obtained in the form of an orange solid,mp 147–148° C.(Dec). The structure is confirmed by the $^1$H-NMR spectrum ($CDCl_3$). δ [ppm]: 6.97 (dd, 1H), 7.30 (dd, 1H), 7.38 (dd, 1H), 7.52 (s, 5H), 7.65 (dd, 1H). $^1$H-NMR reveals the presence of a single isomer.

EXAMPLE 6

(4-Triphenylsilyloxyimino-cyclohexa-2,5-dienylidene)-phenyl-acetonitrile 7 g (31 mmol) of (4-Hydroxyimino-cyclohexa-2,5-dienylidene)-phenyl-acetonitrile, prepared as described in example 1.1, are dissolved in 80 ml of THF and cooled in an ice bath. After adding 10 g (34 mmol) of triphenylchlorosilane to the solution, 4.7 g (47 mmol) of triethylamine are added dropwise, keeping the temperature below 5° C. While the reaction mixture is stirred at 5° C. for 90 min, a precipitate is formed. The precipitate is filtered off and washed with THF. The filtrate is concentrated by a rotary evaporator to afford a red liquid. The residue is diluted with 2-PrOH and stirred at room temperature for 30 min. After cooling the mixture in an ice bath, the solid is isolated by filtration and washed with 2-PrOH. The product is obtained in the form of a pale yellow solid, mp 161–165° C. (Dec). The structure is confirmed by the $^1$H-NMR spectrum ($CDCl_3$). δ [ppm]: 6.79(Z)/6.94(E) (dd, 1H), 7.04(Z)/7.15 (E) (dd, 1H), 7.32–7.71 (m, 22H). $^1$H-NMR reveals that the product is a 77:23 mixture of Z and E isomers. The signals are tentatively assigned to Z and E isomers.

EXAMPLE 7

(5-Diethoxyphosphoryloxyimino-5H-thiophen-2-ylidene)-(2-methylphenyl)-acetonitrile 7.1: (5-Hydroxyimino-5H-thiophen-2-ylidene)-(2-methylphenyl)-acetonitrile 83 ml of 21% $C_2H_5ONa/C_2H_5OH$ solution and 40 ml of toluene are mixed and cooled in an ice-salt bath. To the solution are added 9.0 g (68 mmol) of 2-methylbenzylcyanide in one portion followed by the dropwise addition of 10 g (68 mmol) of 2-nitrothiophene dissolved in 40 ml of toluene over a period of 30 min. The reaction mixture is stirred at −5° C. for 60 min., then poured into 150 ml of water, and acidified with 30 ml of conc. HCl. After separating the organic phase, the aqueous phase is extracted with toluene and the organic extracts are combined. Charcoal is added and the organic phase is stirred for 15 min. After filtering off the charcoal and rinsing with toluene, the filtrate is washed with water and dried over magnesium sulfate. The organic solution is concentrated by a rotary evaporator and the residue is diluted with toluene and stirred at 60° C. for 15 min. The mixture is cooled down in an ice bath and filtered. The product is obtained in the form of a yellow solid, mp 169° C. (Dec). The structure is confirmed by the $^1$H-NMR spectrum ($CDCl_3$). δ [ppm]: 2.37 (s, 3H), 6.11 (d, 1H), 6.90 (d, 1H), 7.20–7.36 (m, 4H), 9.66 (s, 1H).

7.2: (5-Diethoxyphosphoryloxyimino-5H-thiophen-2-ylidene)-(2-methylphenyl)-acetonitrile 8 g (33 mmol) of (5-Hydroxyimino-5H-thiophen-2-ylidene)-(2-methylphenyl)-acetonitrile are dissolved in 90 ml of tetrahydrofuran (THF) and cooled in an ice bath. After adding 6.3 g (36 mmol) of diethylphosphoryl chloride to the solution, 5.0 g (50 mmol) of triethylamine are added dropwise, keeping the temperature below 50° C. The reaction mixture is stirred at 5° C. for 60 min., then poured into 100 ml of water, and extracted with ethyl acetate. The organic phase is washed with 0.1N hydrochloric acid solution, water, and sodium chloride solution. The organic phase is dried over $MgSO_4$, the solvent is distilled off, and the residue is purified by flash chromatography on silica gel with ethyl acetate—hexane (1:1) as eluent. The product is obtained in the form of a yellow solid, melting point 90–91° C. The structure is confirmed by the $^1$H-NMR spectrum ($CDCl_3$). δ [ppm]: 1.43 (t, 6H), 2.37 (s, 3H), 4.36–4.47 (m, 4H), 6.13 (d, 1H), 6.86 (d, 1H), 7.19–7.39 (m, 4H).

EXAMPLE 8

(5-Diphenoxyphosphoryloxyimino-5H-thiophen-2-ylidene)-(2-methylphenyl)-acetonitrile 8 g (33 mmol) of (5-Hydroxyimino-5H-thiophen-2-ylidene)-(2-methylphenyl)-acetonitrile, prepared as described in example 7.1, are dissolved in 90 ml of THF and cooled in an ice bath. After adding 9.8 g (36 mmol) of diphenylphosphoryl chloride to the solution, 5.0 g (50 mmol) of triethylamine are added dropwise, keeping the temperature below 5° C. The reaction mixture is stirred at 50° C. for 20 min, is poured into 100 ml of water, and extracted with ethyl acetate. The organic phase is washed with 0.1N hydrochloric acid solution, water, and sodium chloride solution. The organic phase is dried over $MgSO_4$, the solvent is distilled off, and the residue is purified by flash chromatography on silica gel with ethyl acetate—hexane (1:5) as eluent. The product is obtained in the form of a brown liquid. The structure is confirmed by the $^1$H-NMR spectrum ($CDCl_3$). δ [ppm]: 2.38 (s, 3H), 6.14 (d, 1H), 6.80 (d, 1H), 7.18–7.43 (m, 14H).

EXAMPLE 9

(5-Diethoxythiophosphoryloxyimino-5H-thiophen-2-ylidene)-(2-methylphenyl)-acetonitrile 8 g (33 mmol) of (5-Hydroxyimino-5H-thiophen-2-ylidene)-(2-methylphenyl)-acetonitrile, prepared as described in example 7.1, are dissolved in 90 ml of THF and cooled in an ice bath. After adding 6.9 g (36 mmol) of diethyl chlorothiophosphate to the solution, 5.0 g (50 mmol) of triethylamine are added dropwise, keeping the temperature below 50° C. The reaction mixture is stirred at 50° C. for 60 min, then is poured into 100 ml of water, and extracted with ethyl acetate. The organic phase is washed with 0.1N hydrochloric acid solution, water, and sodium chloride solution. The organic phase is dried over $MgSO_4$, the solvent is distilled off, and the residue is purified by a recrystallization from 2-PrOH. The product is obtained in the form of a brown solid, melting point 86–87° C. The structure is confirmed by the $^1$H-NMR spectrum ($CDCl_3$). δ [ppm]: 1.41 (t, 6H), 2.37 (s, 3H), 4.35–4.46 (m, 4H), 6.13 (d, 1H), 6.85 (d, 1H), 7.19–7.38 (m, 4H).

EXAMPLE 10

(5-Trichloroacetoxyimino-5H-thiophen-2-ylidene)-(2-methylphenyl)-acetonitrile 1.0 g (4.1 mmol) of (5-Hydroxyimino-5H-thiophen-2-ylidene)-(2-methylphenyl)-acetonitrile, prepared as described in example 7.1, are dissolved in 11 ml of THF and cooled in an ice bath. After adding 0.83 g (4.5 mmol) of trichloroacetyl chloride to the solution, 0.63 g (6.2 mmol) of triethylamine are added dropwise, keeping the temperature below 5° C. While the reaction mixture is stirred at 5° C. for 20 min, a precipitate is formed. The precipitate is filtered off and washed with THF. The filtrate is concentrated by a rotary evaporator. The residue is diluted with 2-PrOH and stirred at room temperature for 15 min. After cooling the mixture in an ice bath, the solid is isolated by filtration and washed with 2-PrOH. The product is obtained in the form of a yellow solid, 165° C.(Dec). The structure is confirmed by the $^1$H-NMR spectrum ($CDCl_3$). δ [ppm]: 2.39 (s, 3H), 6.23 (d, 1H), 6.86 (d, 1H), 7.19–7.4 (m, 4H).

EXAMPLE 11

(5-Pentafluorobenzoyloxyimino-5H-thiophen-2-ylidene)-(2-methylphenyl)-acetonitrile 8.0 g (33 mmol) of (5-Hydroxyimino-5H-thiophen-2-ylidene)-(2-methylphenyl)-acetonitrile, prepared as described in example 7.1, are dissolved in 90 ml of THF and cooled in an ice bath. After adding 8.4 g (36 mmol) of pentafluorobenzoyl chloride to the solution, 5.0 g (50 mmol) of triethylamine are added dropwise, keeping the temperature below 5° C. The reaction mixture is stirred at 5° C. for 30 min and then is poured into 100 ml of water. The solid is filtered and rinsed with ethyl acetate. The crude product is purified by recrystallization from 1,2-dichloroethane to afford yellow crystals, mp 204° C. (Dec). The structure is confirmed by the $^1$H-NMR spectrum ($CDCl_3$). 3 [ppm]: 2.38 (s, 3H), 6.21 (d, 1H), 6.85 (d, 1H), 7.19–7.39 (m, 4H).

EXAMPLE 12

(5-Diphenylphosphoryloxyimino-5H-thiophen-2-ylidene)-(2-methylphenyl)-acetonitrile 4.7 g (20 mmol) of (5-Hydroxyimino-5H-thiophen-2-ylidene)-(2-methylphenyl)-acetonitrile, prepared as described in example 7.1, are dissolved in 50 ml of THF and cooled in an ice bath. After adding 5.1 g (21 mmol) of diphenylphosphinic chloride to the solution, 3.0 g (29 mmol) of triethylamine are added dropwise, keeping the temperature below 5° C. The reaction mixture is stirred at 5° C. for 30 min. The reaction mixture is poured into 50 ml of water, and filtered off. The yellow solid is washed with 50 ml of water and 50 ml of a mixture of water and $CH_3OH$ (10:1). The product is purified by the recrystallization from 2-PrOH to afford a yellow solid, mp 165–167° C.(Dec). The structure is confirmed by the $^1$H-NMR spectrum ($CDCl_3$). δ [ppm]: 2.31 (s, 3H), 6.09 (d, 1H), 6.82 (d, 1H), 7.12–7.35 (m, 4H), 7.48–7.65 (m, 6H), 7.95–8.04 (m, 4H).

EXAMPLE 13

(4-Diethoxyphosphoryloxyimino-cyclohexa-2,5-dienylidene)-3,4-dimethoxyphenyl-acetonitrile 13.1: (4-Hydroxyimino-cyclohexa-2,5-dienylidene)-3,4-dimethoxyphenyl-acetonitrile: 241.3 g (4.3 mol) of KOH are dissolved in 1200 ml of methanol and heated up to 55° C. To the solution are added 191.4 g (1.08 mol) of homoveratronitrile, followed by 123.11 g (1.0 mol) of nitrobenzene. The reaction mixture is stirred at 55° C. for 4 h. After cooling, 400 ml of water are added with stirring to the dark reddish solution. The resulting solution is acidified by addition of 440 ml of acetic acid, affording an orange-red suspension. This mixture is filtered, and the red solid is washed with a mixture of methanol and water. The product is dried under vacuum to give 227.5 g of the crude material as an orange solid. After recrystallization from 2000 ml isopropanol, 144 g (51%) of (4-hydroxyimino-cyclohexa-2,5-dienylidene)-3,4-dimethoxyphenyl-acetonitrile are obtained as an orange solid, having a melting point (mp) of 152–154° C. The structure is confirmed by the $^1$H-NMR spectrum (CDCl$_3$, δ [ppm]): 7.5–6.8, m, 7H; 3.92, 3.90 (s, 3H, (E)/(Z) isomers); 3.85, 3.84 (s, 3H, (E)/(Z) isomers). The $^1$H-NMR reveals that the product is approximately a 50:50 mixture of Z and E isomers.
Elemental analysis: C$_{16}$H$_{14}$N$_2$O$_3$ (282.2)

|  | C [%] | H [%] | N [%] |
|---|---|---|---|
| calculated | 68.08 | 5.00 | 9.92 |
| found | 68.01 | 5.18 | 9.60 |

13.2: (4-Diethoxyphosphoryloxyimino-cyclohexa-2,5-dienylidene)-3,4-dimethoxyphenylacetonitrile 6 g (0.021 mol) of (4-Hydroxyimino-cyclohexa-2,5-dienylidene)-3,4-dimethoxyphenyl-acetonitrile are suspended in 50 ml of bromtrichloromethane in a 350 ml round flask. 1 g of triethylphosphite is added to this suspension and the reaction mixture is stirred at room temperature for 60 minutes. Another 6.1 g of triethyliphosphite is added after this time a nd the reaction mixture is stirred overnight. When no more starting material is detected by Thin Layer Chromatography (TLC), the solvent is distilled off, the residue dissolved in dichloromethan and washed with 5% caustic soda and water. Drying of the organic solution over magnesium sulfate and evaporation of the solvent in the rotavap affords 10.3 g of the crude product as a red oil. This oil is further purified by flash chromatography (silica gel, eluent hexane/ethyl acetate 1:1) to give 3.6 g (41%) of (4-diethoxyphosphoryloxyimino-cyclohexa-2,5-dienylidene)-3,4-dimethoxypheenyl-acetonitrile as a red oil. $^{31}$P-NMR (CDCl$_3$; δ relative to H$_3$PO$_4$ as external reference): 0.147 and 0.009 ppm (P(V)of the (E)land (Z)-isomers). $^1$H-NMR (CDCl$_3$, δ [ppm]): 7.55–7.20 (m, 3H); 7.1–6.8 (m, 3H), 4.40–4.20, (m, 4H-C(1')); 3.98 and 3.96 (s, CH$_3$O—C(4), (E) and (Z) isomers; 3.95 and 3.93 (s, CH$_3$O—C(3), (E) and (Z) isomers); 1.37 and 1.36 (t, 3H-C(2')).
Elemental analysis: C$_{20}$H$_{23}$O$_6$N$_2$P (418.38)

|  | C [%] | H [%] | N [%] |
|---|---|---|---|
| calculated | 57.42 | 5.54 | 6.70 |
| found | 57.67 | 5.60 | 6.48 |

EXAMPLE 14

(4-Diethoxyphosphoryloxyimino-cyclohexa-2,5-dienylidene)-2,4-dichlorophenyl-acetonitrile 14.1: (4-Hydroxyimino-cyclohexa-2,5-dienylidene)-2,4-dichlorphenyl-acetonitrile: 99.9 g (1.78 mol) of KOH are dissolved in 600 ml of methanol and heated up to 55° C. To the solution are added 1d00 g (0.538 mol) of 2,4-dichlorphenylacetonitril, followed by 60.2 g (0.489 mol) of nitrobenzene. The reaction mixture is stirred at 559° C. for 4 h. After cooling, 800 ml of water are added with stirring. The resulting solution is acidified by addition of 212.8 g of acetic acid and 200 ml of water, affording a yellowish suspension. This mixture is filtered, and the yellow solid is washed with a mixture of methanol and water. The crude product is dried under vacuum. After recrystallization from 2000 ml of toluene, 74.3 g (52%) of (4-hydroxyimino-cyclohexa-2,5-dienylidene)-2,4-dichlorphenyl-acetonitrile are obtained as a yellowish solid, having a melting point (mp) of 160–161° C. The structure is confirmed by the $^1$H-NMR spectrum (CDCl$_3$, δ [ppm]): 7.6–7.2 (m, 5H); 6.95–6.5 (m, 2H); 5.8 (broad s, OH).
Elemental analysis: C$_{14}$H$_8$Cl$_2$N$_2$O(291.12)

|  | C [%] | H [%] | N [%] |
|---|---|---|---|
| calculated | 57.76 | 2.77 | 9.62 |
| found | 57.58 | 2.59 | 9.45 |

14.2: (4-Diethoxyphosphoryloxyimino-cyclohexa-2,5-dienylidene)-2,4-dichlorophenyl-acetonitrile:

20.4 g (0.07 mol) of (4-hydroxyimino-cyclohexa-2,5-dienylidene)-2,4-dichlorphenyl-acetonitrile, 7.1 g (0.07 mol) of triethylamine and a catalytic amount of N,N-dimethylaminopyridine are dissolved in 270 ml of THF. This solution is cooled in an ice bath, and 12.1 g (0.07 mol) of diethylphosphoryl chloride are added dropwise while stirring. When the addition is complete, the orange solution is warmed to room temperature and stirred overnight. Water and ethyl acetate are subsequently added, and the organic layer is washed several times with saturated sodium chloride solution and water and dried over magnesium sulfate. Evaporation of the solvent gives 30.4 g of a viscous yellowish oil, which is further purified by filtration over silica gel (eluent: hexane/ethyl acetate 9:1). Yield: 25.5 g (85%). $^{31}$P-NMR (CDCl$_3$; δ relative to H$_3$PO$_4$ as external reference): 0.132 and 0.003 ppm (P(V) of the (E) and (Z)-isomers). $^1$H-NMR (CDCl$_3$, δ [ppm]): 7.60–7.15 (m, 7H); 7.0–6.55 (m, 2H), 4.35–4.15, (m, 4H-C(1')); 1.38 and 1.35 (t, 3H-C(2')).
Elemental analysis: C$_{18}$H$_{17}$Cl$_2$N$_2$O$_4$P (427.20)

|  | C [%] | H [%] | N [%] |
|---|---|---|---|
| calculated | 50.61 | 4.01 | 6.56 |
| found | 50.42 | 4.31 | 6.24 |

EXAMPLE 15

(4-Diphenylphosphoryloxyimino-cyclohexa-2,5-dienylidene)-3,4-dimethoxyphenyl-acetonitrile 10.16 g (0.036 mol) of (4-Hydroxyimino-cyclohexa-2,5-dienylidene)-3,4-dimethoxyphenylacetonitrile (prepared as described in Example 13.1) and 3.64 g (0.036 mol) of triethylamine are dissolved in 180 ml of tetrahydrofuran and cooled to 0–5° C. 8.52 g (0.036 mol) of diphenylphosphoryl chloride, dissolved in 70 ml of tetrahydrofuran, are added dropwise. When the addition is completed, the ice bath is removed and the solution stirred overnight at room temperature. Water and ethyl acetate are subsequently added, the organic layer is washed several times with saturated sodium chloride solution and water and dried over magnesium sulfate. Evaporation of the solvent gives 20.7 g of a viscous red oil, which is further purified by filtration over silica gel (eluent: hexane/ethyl acetate 9:1). Yield: 11.5 g (62%) (4-diphenylphosphoryloxyimino-cyclohexa-2,5- dienylidene)-3,4-dimethoxyphenyl-acetonitrile, reddish viscous oil which solidifies upon standing. $^{31}$P-NMR (CDCl$_3$; δ relative to H$_3$PO$_4$ as external reference): 37.102 and 2.9.092 ppm (P(V) of the (E) and (Z)-isomers). $^1$H-NMR (CDCl$_3$, δ [ppm]): 7.9–7.75 (m, 4H); 7.55–7.35 (m, 6H), 7.4–6.65 (m, 7H); 3.91/3.90 (s, 3H, (E)/(Z) isomers); 3.89/3,88 (s, 3H, (E)/(Z) isomers).

Elemental analysis: C$_{28}$H$_{23}$N$_2$O$_4$P (482.48)

|  | C [%] | H [%] | N [%] |
|---|---|---|---|
| calculated | 69.70 | 4.81 | 5.81 |
| found | 69.94 | 4.67 | 6.02 |

EXAMPLE 16

Preparation of a Negative Resist

A resist solution is prepared by dissolving 65 parts of polyvinylphenol (Mw =4.000, Maruzen Chemicals Co. Ltd.), 30 parts of hexa(methoxymethyl)melamin (Cymel® 303, Cyanamid) and 5 parts of the latent acid to be tested in 7.5 g of propylene glycol 1-monomethylether 2-acetate, which contains 1000 ppm of an anti-foaming agent (FC430). This solution is spincoated onto the polished side of a silicon wafer (diameter 4 inches), which has been pretreated with hexamethyidisilazane, by spinning at 5000 rpm for 30 seconds. The solvent is removed by drying the coated wafer for 60 seconds at 110° C. on a hot plate (pre-bake), which results in films of 1 μm thickness. Irradiation of the samples is performed with a Canon mask aligner (Canon PLA 501) using interference filters to select the wavelengths at 365, 405 and 436 nm. For each wavelength a fixed dose is used, but due to the lower output of the lamp and absorption of the latent acid, longer irradiation times respectively higher doses are used at longer wavelength in order to achieve sufficient crosslinking. A special mask containing a grey-scale step wedge (transmissions ranging from 0 to 50%) and resolution patterns are used. After exposure the wafers are heated for 60 seconds to 110° C. to perform the post exposure bake (PEB) during which the liberated acid catalyses the crosslinking reaction in the irradiated areas. Developing is performed by dipping the samples into a 2.38% solution of tetramethyl ammonium hydroxide (TMAH) for 60 seconds. The thickness of the film before exposure as well as after exposure in the fields that were exposed to different doses is measured with an Axiotron (Zeiss) which uses white light interference. The thickness measurements are used to estimate the one-to-one energy E1:1 which is the dose that is required to retain the same film thickness as before developing. The film thickness o f the cured samples is also measured by means of an Alpha Step profilometer.

The step with the highest number that is cured is used to calculate the minimum dose E0 required to have crosslinking. The smaller the required dose the more reactive is the latent acid.

The results are listed in Table 1 and show that the latent acids have high sensitivity in a negative resist at all wavelengths.

TABLE 1

| Latent acid compound of example | Reactivity at 365 nm (mJ/cm$^2$) | | Reactivity at 405 nm (mJ/cm$^2$) | | Reactivity at 436 nm (mJ/cm$^2$) | |
|---|---|---|---|---|---|---|
| 1 | E0 | 80 | E0 | 270 | E0 | >1000 |
|   | E1:1 | 120 | E1:1 | 350 | E1:1 | >1000 |
| 2 | E0 | 14 | E0 | 54 | E0 | >1000 |
|   | E1:1 | 18 | E1:1 | 55 | E1:1 | >1000 |
| 7 | E0 | 28 | E0 | 21 | E0 | 28 |
|   | E1:1 | 50 | E1:1 | 35 | E1:1 | 38 |
| 8 | E0 | 9 | E0 | 7 | E0 | 7 |
|   | E1:1 | 22 | E1:1 | 16 | E1:1 | 10 |
| 12 | E0 | >1000 | E0 | 230 | E0 | 230 |
|   | E1:1 | >1000 | E1:1 | 340 | E1:1 | 340 |

What is claimed is:

1. Compounds of formulae I or II

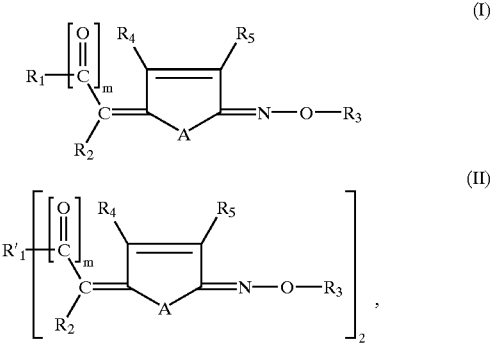

wherein m is 0 or 1;

R$_1$ is phenyl which is unsubstituted or substituted by one or more of the radicals C$_1$–C$_{12}$alkyl, C$_1$–C$_4$haloalkyl, halogen, phenyl, OR$_6$, NR$_7$R$_8$, SR$_9$ and/or —S-phenyl, optionally the substituents OR$_6$, SR$_9$ or NR$_7$R$_8$ form 5- or 6-membered rings, via the radicals R$_6$, R$_7$, R$_8$ and/or R$_9$, with further substituents on the phenyl ring or with one of the carbon atoms of the phenyl ring, or R$_1$ is naphthyl, anthracyl or phenanthryl, the radicals naphthyl, anthracyl and phenanthryl being unsubstituted or substituted by C$_1$–C$_6$alkyl, phenyl, OR$_6$, NR$_7$R$_8$, SR$_9$ and/or —S-phenyl, optionally the substituents OR$_6$, SR$_9$ or NR$_7$R$_8$ form 5- or 6-membered rings, via the radicals R$_6$, R$_7$, R$_8$ and/or R$_9$ with further substituents on the naphthyl, anthracyl or phenanthryl ring or with one of the carbon atoms of the naphthyl, anthracyl or phenanthryl ring, or R$_1$ is a heteroaryl radical which is unsubstituted or substituted by C$_1$–C$_6$alkyl, phenyl, OR$_6$, NR$_7$R$_8$, SR$_9$ and/or —S-phenyl, optionally the substituents OR$_6$, SR$_9$ or NR$_7$R$_8$ form 5- or 6-membered rings, via the radicals R$_6$, R$_7$, R$_8$ and/or R$_9$ with further substituents on the heteroaryl ring or with one of the carbon atoms of the heteroaryl ring, or, if m is 0, R$_1$ additionally is $C_2$–$C_6$alkoxycarbonyl, phenoxycarbonyl, CN, hydrogen or $C_1$–$C_{12}$ alkyl;

$R'_1$ is $C_2$–$C_{12}$alkylene, phenylene, naphthylene,

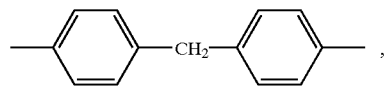

diphenylene or oxydiphenylene, these radicals being unsubstituted or substituted by $C_1$–$C_{12}$alkyl;

$R_2$ is CN;

n is 1 or 2;

$R_3$ is $C_2$–$C_6$haloalkanoyl, halobenzoyl, or a group

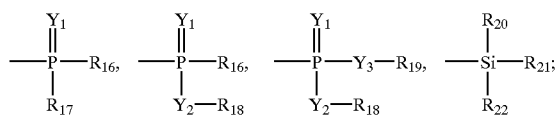

$Y_1$, $Y_2$ and $Y_3$ are independently of each other O or S;

$R_4$ and $R_5$ are independently of each other hydrogen, halogen, $C_1$–$C_6$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_6$, $SR_9$, $NR_7R_8$, $C_2$–$C_6$alkoxycarbonyl, phenoxycarbonyl, $S(O)_nC_1$–$C_6$alkyl, $S(O)_nC_6$–$C_{12}$aryl, $C_1$–$C_{12}$alkylsubstituted $S(O)_nC_6$–$C_{12}$aryl, $SO_2O$—$C_1$–$C_6$alkyl, $SO_2O$–$C_6$–$C_{10}$aryl or $NHCONH_2$, or $R_4$ and $R_5$ together are —$C(R_{12})$=$C(R_{13})$—$C(R_{14})$=$C(R_{15})$—;

$R_5$ is hydrogen, phenyl; $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl; or $R_6$ is $C_2$–$C_{12}$alkyl interrupted by —O—, optionally substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

$R_7$ and $R_8$ are independently of each other hydrogen; $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_7$ and $R_8$ are $C_2$–$C_{12}$alkyl interrupted by —O—, optionally substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_7$ and $R_8$, together with the nitrogen atom to which they are bound, form a 5-, 6- or 7-membered ring which optionally is interrupted by —O— or by —$NR_{7a}$-;

$R_{7a}$ is hydrogen, phenyl; $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl; or $R_{7a}$ is $C_2$–$C_{12}$alkyl interrupted by —O—, optionally substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl; or $R_{7a}$ is phenyl, $C_2$–$C_6$alkanoyl, benzoyl, $C_1$–$C_6$alkylsulfonyl, phenylsulfonyl, (4-methylphenyl) sulfonyl, naphthylsulfonyl, anthracylsulfonyl or phenanthrylsulfonyl;

$R_9$ is $C_1$–$C_{12}$alkyl which is unsubstituted or substituted by OH and/or $C_1$–$C_4$alkoxy; or $C_2$–$C_{12}$alkyl interrupted by —O—, soptionally substituted by OH and/or $C_1$–$C_4$alkoxy;

A is S, O, $NR_{7a}$, or a group of formula A1, A2, A3 or A4

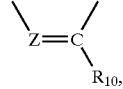
(A1)

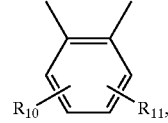
(A2)

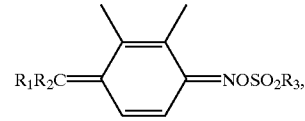
(A3)

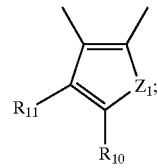
(A4)

$R_{10}$ and $R_{11}$ independently of each other have one of the meanings given for $R_4$, or $R_{10}$ and $R_{11}$ together are —CO—$NR_{7a}CO$—, or $R_{10}$ and $R_{11}$ together are —$C(R_{12})$=$C(R_{13})$—$C(R_{14})$=$C(R_{15})$—;

$R_{12}$, $R_{13}$, $R_{14}$ and $R_{15}$ independently of one another are hydrogen, $C_1$–$C_4$alkyl, halogen, phenyl, $OR_6$, $SR_9$, $NR_7R_8$, —S-phenyl, $C_2$–$C_6$alkoxycarbonyl, phenoxycarbonyl, CN, $NO_2$, $C_1$–$C_4$haloalkyl, $S(O)_n$ $C_1$–$C_6$alkyl, $S(O)_nC_6$–$C_{12}$aryl, $C_1$–$C_{12}$alkyl-substituted $S(O)_nC_6$–$C_{12}$aryl, $SO_2O$—$C_1$–$C_6$alkyl, $SO_2O$—$C_6$–$C_{10}$aryl or $NHCONH_2$;

$R_{16}$ and $R_{17}$ independently of each other are $C_1$–$C_6$alkyl which is unsubstituted or substituted by halogen; or are phenyl which is unsubstituted or substituted by $C_1$–$C_4$alkyl or halogen;

$R_{18}$ and $R_{19}$ independently of each other have one of the meanings of $R_{16}$, or $R_{18}$ and $R_{19}$, or together are 1,2-phenylene or $C_2$–$C_6$alkylene which is unsubstituted or substituted by $C_1$–$C_4$alkyl or halogen;

$R_{20}$, $R_{21}$ and $R_{22}$ independently of each other are $C_1$–$C_6$alkyl which is unsubstituted or substituted by halogen; or are phenyl which is unsubstituted or substituted by $C_1$–$C_4$alkyl or halogen; or $R_{21}$ and $R_{22}$ together are 2,2'-biphenylene or $C_2$–$C_6$alkylene which is unsubstituted or substituted by $C_1$–$C_4$alkyl or halogen;

Z is $CR_{11}$ or N; and $Z_1$ is —$CH_2$—, S, O or $NR_{7a}$.

2. Compounds according to claim 1 of formulae I and II, wherein m is 0;

$R_1$ is phenyl which is unsubstituted or substituted by $C_1$–$C_6$alkyl, phenyl, $OR_6$, $SR_9$, —S-phenyl, halogen and/or by $NR_7R_8$; optionally the substituents $OR_6$, or $NR_7R_8$ form 5- or 6-membered rings, via the radicals $R_6$, $R_7$ and/or $R_9$ with further substituents of the phenyl ring, or with one of the carbon atoms of the phenyl ring; $R'_1$ is phenylene, naphthylene,

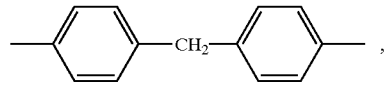

diphenylene or oxydiphenylene, these radicals being unsubstituted or substituted by $C_1$–$C_{12}$alkyl.

3. Compounds according to claim 1, of the formula Ia

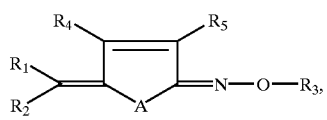

(Ia)

wherein $R_1$, $R_2$, $R_3$, $R_4$, $R_5$ and A are as defined in claim 1.

4. Compounds according to claim 3, of the formula Ia, wherein
$R_3$ is a group

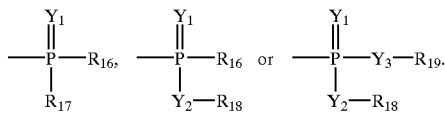

5. Compounds according to claim 3, of the formula Ia, wherein
$R_1$ is phenyl which is unsubstituted or substituted once or twice by $C_1$–$C_4$alkyl, $OR_6$ or halogen;
$R_2$ is CN;
$R_3$ is $C_2$–$C_6$haloalkanoyl, halobenzoyl, or a group

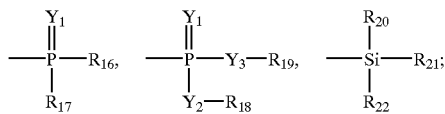

$Y_1$, $Y_2$ and $Y_3$ are independently of each other O or S;
$R_4$ and $R_5$ are hydrogen;
$R_6$ is $C_1$–$C_3$alkyl
A is —S— or a group of the formula $A_1$

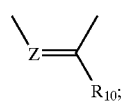

Z is $CR_{11}$;
$R_{10}$ and $R_{11}$ are hydrogen;
$R_{16}$ and $R_{17}$ independently of each other are phenyl;
$R_{18}$ and $R_{19}$ independently of each other are $C_1$–$C_6$alkyl or phenyl; and
$R_{20}$, $R_{21}$ and $R_{22}$ are phenyl.

6. A composition comprising
a) at least one compound which can be crosslinked under the action of an acid and/or
b) at least one compound the solubility of which is altered under the action of an acid and
c) as latent acid photoinitiator, at least one compound of formula I or II according to claim 1.

7. A composition according to claim 6, which comprises in addition to component c) further photoinitiators, sensitisers and/or additives.

8. A method of crosslinking compounds which can be crosslinked under the action of an acid, which method comprises irradiating a composition according to claim 7 imagewise or over the whole area with light having a wavelength of 180–1500 nm.

9. A method of crosslinking compounds which can be crosslinked under the action of an acid, which method comprises irradiating a composition according to claim 6 imagewise or over the whole area with light having a wavelength of 180–1500 nm.

10. A method for the preparation of surface coatings, printing inks, printing plates, dental compositions, colour filters, resist materials and as image-recording material, or image-recording material for recording holographic images, which comprises irradiating a composition according to claim 6 with light having a wavelength of 180–1500 nm.

11. A method for the preparation of surface coatings, printing inks, printing plates, dental compositions, colour filters, resist materials and as image-recording material, or image-recording material for recording holographic images, which comprises irradiating a composition according to claim 7 with light having a wavelength of 180–1500 nm.

12. A photoresist based on oxime compounds as photosensitive acid donors, the photoresist comprising as oxime compound a compound of formula I and/or II according to claim 1.

13. A photoresist according to claim 12, which photoresist is a negative resist.

14. A photoresist according to claim 12, which photoresist is a positive resist.

15. A photoresist according to claim 12, which photoresist is a chemically amplified resist.

16. A photoresist according to claim 12, comprising polymers that are transparent down to the wavelength region of 180 nm.

17. A process for the preparation of a photoresist, comprising
(1) applying to a substrate a composition according to claim 6;
(2) optionally heating to remove a solvent from the composition:
(3) image-wise irradiating with light of wavelengths between 150 and 1500 nm;
(4) thermally treating the irradiated composition; and
(5) removing the non-cured areas by development and thus achieving a patterned coating.

* * * * *

UNITED STATES PATENT AND TRADEMARK OFFICE
CERTIFICATE OF CORRECTION

PATENT NO. : 6,485,886 B1 Page 1 of 1
APPLICATION NO. : 09/830248
DATED : November 26, 2002
INVENTOR(S) : Hitoshi Yamato et al.

It is certified that error appears in the above-identified patent and that said Letters Patent is hereby corrected as shown below:

On the title page, Item (86) should read:

-- (86) PCT No.     PCT/EP99/07876
        § 371 (c)(1),
        (2), (4) Date: Apr. 24, 2001 --.

Signed and Sealed this

Seventeenth Day of April, 2007

JON W. DUDAS
*Director of the United States Patent and Trademark Office*